(12) United States Patent
Pereira et al.

(10) Patent No.: US 7,354,900 B2
(45) Date of Patent: Apr. 8, 2008

(54) TREATMENT AND INHIBITION OF OCULAR INFECTIONS AND WOUNDS BY CAP37 AND CAP37 PEPTIDES

(75) Inventors: Heloise Anne Pereira, Edmond, OK (US); James Chodosh, Edmond, OK (US); Michelle C. Callegan, Edmond, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 361 days.

(21) Appl. No.: 10/423,311

(22) Filed: Apr. 25, 2003

(65) Prior Publication Data
US 2003/0206938 A1 Nov. 6, 2003

Related U.S. Application Data

(60) Provisional application No. 60/378,295, filed on May 3, 2002.

(51) Int. Cl.
*A61K 38/16* (2006.01)
*A61K 9/00* (2006.01)
(52) U.S. Cl. .................... 514/12; 530/326; 530/324; 530/350; 530/402; 424/9.1
(58) Field of Classification Search ............. 530/326, 530/350, 324, 335, 402; 514/12; 424/9.1
See application file for complete search history.

(56) References Cited

U.S. PATENT DOCUMENTS

| 5,458,874 A | 10/1995 | Pereira et al. | |
|---|---|---|---|
| 5,484,885 A | 1/1996 | Pereira et al. | |
| 5,515,117 A * | 5/1996 | Dziabo et al. | 351/160 H |
| 5,607,916 A | 3/1997 | Pereira et al. | |
| 5,627,262 A | 5/1997 | Pereira | |
| 5,650,392 A | 7/1997 | Pereira et al. | |
| 5,877,151 A | 3/1999 | Pereira | |
| 6,071,879 A | 6/2000 | Pereira | |
| 6,107,460 A * | 8/2000 | Pereira | 530/326 |
| 6,482,799 B1 * | 11/2002 | Tuse et al. | 514/14 |
| 6,696,238 B2 * | 2/2004 | Murphy et al. | 435/1.1 |
| 6,872,705 B2 * | 3/2005 | Lyons | 514/13 |

FOREIGN PATENT DOCUMENTS

| WO | WO 93/19087 | 9/1993 |
|---|---|---|
| WO | WO 02/09738 A1 | 2/2002 |
| WO | PCT/US03/13146 | 3/2005 |

OTHER PUBLICATIONS

Paulsen et al. Detection of natural peptide antibiotics in human nasolacrimal ducts.Sep. 2001. Investigative ophthalmology & visual science, vol. 42 (10), pp. 2157-2163.*
Schwab et al. Corneal storage medium preservation with defensins. 1992. Cornea, vol. 11(5), pp. 370-375.*
Baum, J., "Infections of the eye", *Clinical Infectious Diseases*, 1995; 21:479-488.
Brennan, NA, et al., "Extended wear in perspective", *Optometry and Vision Science*, 1997; 74:609-623.
Gritz, DC, et al., "Topical issues in the treatment of bacterial keratitis", *International Ophthalmology Clinics*, 1998; 38(a):107-116.
Hammond, RW, et al., "Treatment of ocular bacterial infections: an update", *Journal of the American Optometric Association*, 1997; 68"178-187.
Levine, J, et al., "Practical ophthalmic microbiology", *Journal of Ophthalmic Nursing & Technology*, 1999; 18:50-59.
Marone, P, et al., "Ocular infections: antibiotics and bacterial adhesion on biomaterials used in ocular surgery", *Ophthalmologica*, 1995; 209:315-318.
McLaughlin-Borlace, L, et al., "Bacterial biofilm on contact lenses and lens storage cases in wearers with microbial keratitis", *Journal of Applied Microbiology*, 1998; 84:827-838.
Snyder, RW, "Antibiotic therapy for ocular infection", *West J. Med.*, 1994; 161:579-584.
Ruan, et al., "Corneal Expression of the Inflammatory Mediator CAP37", Investigative Ophthalmology & Visual Science, May 2002, vol. 43, No. 5, pp. 1414-1421, XP009018927 (the whole document).
Ruan, et al., "Expression of CAP37, a multifunctional inflammatory mediator, in corneal epithelial cells in a rabbit model of *Staphylococcus aureus* keratitis", Investigative Ophthalmology & Visual Science, Mar. 15, 1999, vol. 40, No. 4, p. S261, XP009018930, Annual Meeting of the Association for Research in Vision and Ophthalmology; Fort Lauderdale, Florida, USA; May 9-14, 1999 abstract.
Ruan, et al., "Induction and molecular cloning of CAP37, a novel inflammatory mediator from corneal epithelial cells", Investigative Ophthalmology & Visual Science, Mar. 15, 2000, vol. 41, No. 4, p. S905, XP009018929, Annual Meeting of the Association in vision and Ophthalmology; Fort Lauderdale, Florida, USA; Apr. 30-May 5, 2000, abstract.

(Continued)

*Primary Examiner*—Chih-Min Kam
(74) *Attorney, Agent, or Firm*—Dunlap, Codding & Rogers, P.C.

(57) ABSTRACT

A method for treating ocular conditions such as bacterial keratitis, bacterial conjunctivitis, corneal ulcers and wounds, endophthalmitis, and blebitis in mammals, by using a native, synthetic, or recombinant CAP37, or effective peptide portions thereof including CAP37 peptides 20-44, 23-42, 102-122, and 120-146 and monocysteine derivatives of peptides 20-44 and 23-42. The CAP37, peptides, and peptide derivatives can also be used to store, clean, sterilize, or coat contact lenses, and may be used in media for storing mammalian corneal transplants.

10 Claims, 11 Drawing Sheets

OTHER PUBLICATIONS

Periera, et al., "Modulation of Adhesion Molecule Expression on Human Corneal Epithelial Cells (HCEC) by the Inflammatory Mediator, CAP37", Database Biosis 'Online! Biosciences Information Service, Philadelphia, PA, US; 2002, Database accession No. PREV200300165534, XP002258533. abstract, & Arvo Annual Meeting Abstract Search and Program Planner, vol. 2002, 2002, page Abstract No. 4201 Annual Meeting of the Association For Research in Vision and Ophthalmology; Fort Lauderdale, Florida, USA; May 5-10, 2002.

Paulsen et al., "Detection of Natural Peptide Antibiotics in Human Nasolacrimal Ducts," Investigative Ophthalmology & Visual Science, Sep. 2001, vol. 42, No. 10, pp. 2157-2163.

Cochereau-Massin et al., "Efficacy and Ocular Penetration of Sparfloxacin in Experimental Streptococcal Endophthalmitis", Antimicrobial Agents and Chemotherapy, American Society for Microbiology, Apr. 1993, p. 633-636, vol. 37, No. 4.

Ferencz et al., "Archives of Ophthalmology, Arch Ophthalmol", Aug. 1999, p. 1023-1027, vol. 117(8).

El-Massry et al., "Aminoglycoside Levels in the Rabbit Vitreous Cavity after Intravenous Administration", American Journal of Ophthalmology, Nov. 1996, p. 122: 684-689, vol. 122 No. 5.

* cited by examiner

TREATMENT AND INHIBITION OF OCULAR INFECTIONS AND WOUNDS BY CAP37 AND CAP37 PEPTIDES

CROSS REFERENCE TO RELATED APPLICATIONS

This application claims the benefit of U.S. Serial No. 60/378,295, filed May 3, 2002, which is hereby expressly incorporated herein by reference in its entirety.

STATEMENT REGARDING FEDERALLY SPONSORED RESEARCH OR DEVELOPMENT

Some aspects of this invention were made in the course of Grant AI 28018 awarded by the National Institutes of Health and therefore the Government has certain rights in some aspects of this invention.

BACKGROUND

Ocular infections such as bacterial keratitis are serious clinical problems. Bacterial keratitis, for example, is a component of many ocular infections, especially among those who have sustained penetrating corneal injuries, used extended-wear contact lenses, undergone incisional refractive surgery, or are immunocompromised. Bacterial keratitis is an important cause of visual morbidity. Contact lens wearers are most at risk. More recently, the use of refractive correction in the form of incisional and laser surgery has emerged as a new cause of bacterial keratitis (1-4). Loss of vision and permanent scarring are commonly due to toxic bacterial products and the host inflammatory response to wounding and infection. Common causative organisms are the Gram positive bacteria *Staphylococcus aureus* and the Gram negative bacterium *Pseudomonas aeruginosa* (5-7). The bacterial products and toxins and host inflammatory reaction stimulated in response to wounding and infection often leads to extensive tissue damage with permanent scarring and irreversible loss of vision (1).

Current treatments include the use of broad spectrum antibiotics. Topical antibiotic drops are the preferred treatment for corneal and conjunctival infections. Intravitreal antibiotics are preferred for endophthalmitis and parenteral antibiotics are recommended for deep infections.

The diagnosis and treatment of bacterial keratitis remains controversial. A combination of a fortified topical cephalosporin and a fortified topical aminoglycoside were once the first line of therapy. However, recently this therapy has been replaced by fluoroquinolones such as ciprofloxacin and ofloxacin for topical ophthalmic therapy. However, the emergence of methicillin-resistant organisms has reduced the effectiveness of these antibiotics. Thus the choice of initial empirical therapy is controversial. Clearly, there is a crisis situation developing with organisms that cause ocular infections which are resistant to antibiotics.

Because early treatment of the infection is important to prevent loss of vision, treatment is generally started before the specific identity of the causative organism and its sensitivity are known. Therefore, a broad spectrum antibiotic is generally used initially. Once the culture results are known the treatment is best modified to a single drug to cover the infectious organisms. It is important that the specific antibiotic have as narrow a spectrum as possible, since broad spectrum agents could unnecessarily alter the normal flora allowing super infection from resistant or nonsusceptible organisms.

Steroid treatment has also been used in conjunction with antibiotics in the hope that it will limit the inflammatory process of the host, however this course of treatment requires careful monitoring.

Almost all topical ophthalmic antibiotics can cause local irritation and allergic reactions. Treatment for severe bacterial keratitis (bacterial corneal ulcer), regardless of the identity of the antimicrobial agent used, typically consists of instillation of drug every 15-30 minutes around the clock for the first 2-3 days. The dosing interval is then gradually increased to every four hours and continued for an additional 14 days. Topical drops are preferred for corneal and conjunctival infections. The agent should be bactericidal rather than bacteriostatic.

The cornea is normally considered a "privileged" site because of its avascularity and lack of lymphatic vessels (8-10). Antigens, cytokines, inflammatory mediators and leukocytes that enter into the cornea must do so from the limbic and/or ciliary body vessels. Inflammatory cytokines and/or chemotactic gradients that are elicited locally by corneal cells could therefore profoundly affect the emigration of leukocytes from the limbic and ciliary circulation to the cornea.

Extravasation of leukocytes from the circulation into tissue sites is an integral feature of the host response to injury and inflammation. By virtue of their ability to engulf and destroy bacteria, eliminate toxins and secrete numerous soluble mediators, leukocytes are capable of restricting and limiting the spread of infection. Neutrophils (PMNs) are the predominant cell type in the early phases of inflammation and are soon followed by a second wave of cells composed mainly of monocytes and lymphocytes. Irreversible damage to the eye can occur in cases of fulminant inflammation. Clearly the desirable outcome is one in which the immune system can control the infection resulting in re-epithelialization and healing with minimum damage to vision.

The identification of a corneal derived chemotaxin or inflammatory mediator could be of extreme importance in our understanding of the mechanisms that regulate leukocyte migration, epithelial-leukocyte interaction, corneal inflammation and healing and in identifying methods of treatment of corneal damage related to infection, inflammation and physical wounding.

SUMMARY OF THE INVENTION

*Pseudomonas aeruginosa* is frequently associated with infection following use of extended-wear contact lenses. The most common organism associated with corneal infection in patients who do not wear contact lenses is *Staphylococcus aureus*. CAP37 is important in the recruitment of leukocytes from the circulation in the limbus of the eye to the avascular cornea. CAP37 proteins and peptides derived therefrom can be used as a topical/oral/intravenous/intravitreal antibiotic for the treatment of ocular bacterial infections in mammals including humans, primates, rabbits, livestock animals and ungulates, for example. CAP37 and CAP37 peptides can also be used to promote healing of corneal wounds and ulcers that may not have an infective component, such as those due to injury by foreign objects or trauma. CAP37 and CAP37 peptides can also be used to treat contact lenses, to sterilize the lenses and inhibit infections caused by bacteria on the lenses. Mammalian corneal transplants can also be stored in media containing CAP37 and/or CAP37 peptides as described herein.

Corneal wound healing consists of three interrelated processes, including corneal epithelial cell proliferation, corneal epithelial cell migration and upregulation of adhesion molecules that are capable of binding to extracellular matrix proteins forming attachments and adhesion and thereby aiding healing. As shown herein, CAP37 promotes corneal epithelial cell proliferation, and migration. Also shown is that CAP37 upregulates corneal epithelial cell adhesion molecules including intercellular adhesion molecule-1 (ICAM-1) and platelet-endothelial cell adhesion molecule-1 (PECAM-1). Both ICAM-1 and PECAM-1 are important in leukocyte-epithelial interactions. Importantly CAP37 upregulates α-3 (CD49c) and β-1 (CD29) integrin molecules. α-3 β-1 integrin molecules are critical for binding of the corneal epithelial cell to laminin-5 and fibronectin two important constituents in the basement membrane of the cornea. Taken together these studies indicate that CAP37 is involved in the promotion of corneal epithelial wound healing.

DETAILED DESCRIPTION OF THE INVENTION

Figure 1:
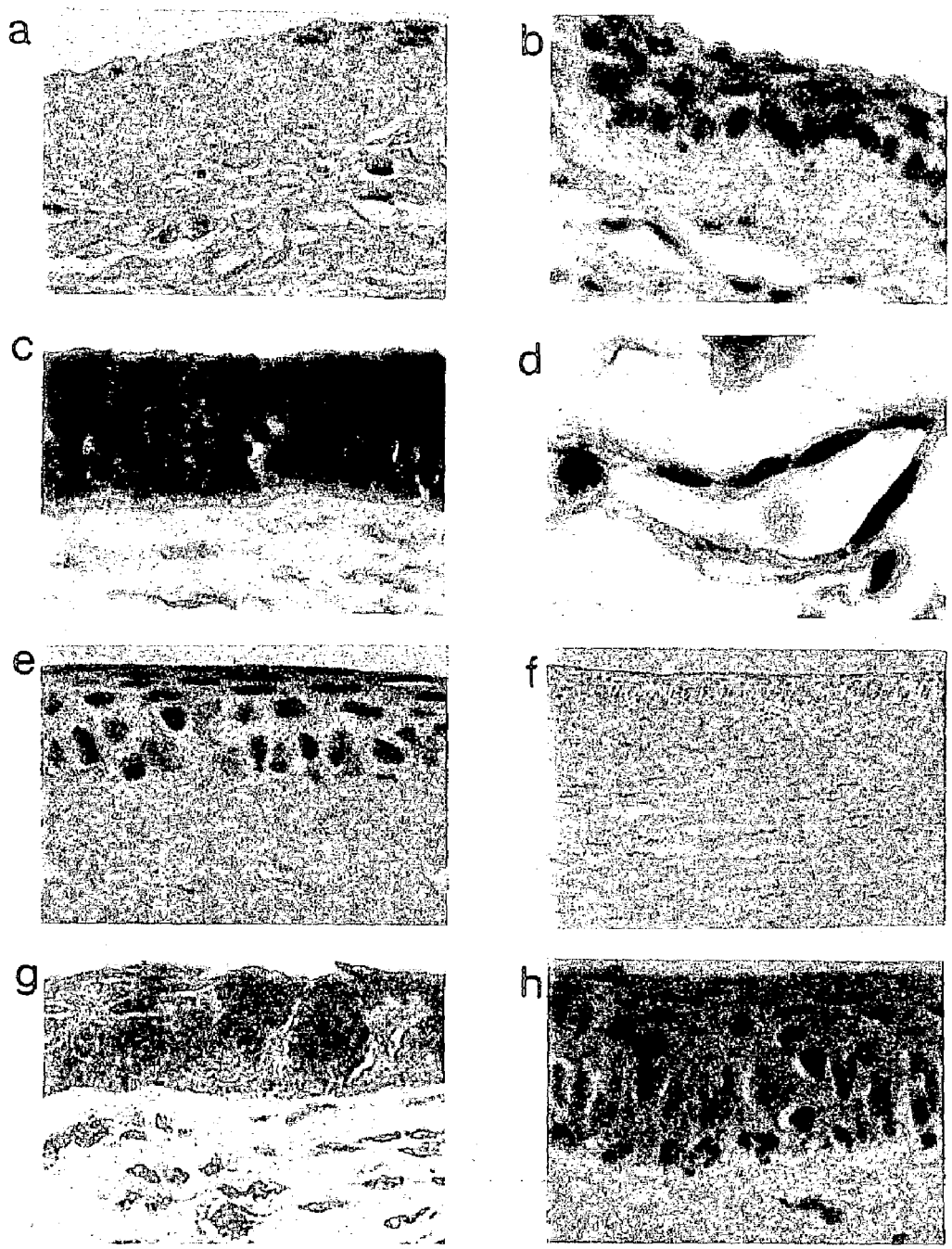
FIG. 1. Ocular localization of CAP37 in response to intrastromal injection of S. aureus in the rabbit eye-model of bacterial keratitis. (a) A representative photomicrograph of the junction between ocular conjunctiva and cornea at 5 hr post infection. Immunohistochemical staining using mouse anti-CAP37 and the Vectastain ABC-peroxidase technique indicating faint staining for CAP37 in the conjunctival epithelium and relatively weaker staining for CAP37 in corneal epithelium. Note absence of staining in vascular endothelium, ×400 (b) Sham-injected rabbit eye at 5 hr stained with mouse anti-CAP37 antiserum indicating absence of staining for CAP37 in ocular tissue, ×400 (c) Immunohistochemical staining for CAP37 using mouse anti-CAP37 antiserum at 10 hr post infection showing strong reaction for CAP37 in corneal epithelium, ×400 (d) Strong staining for CAP37 in endothelial cells lining a vessel located in the ciliary body at 10 hr post infection. Also note staining for PMN, ×1000 (e) Specificity control using normal mouse serum to stain tissue from a rabbit 10 hr post infection, ×400 (f) Absence of staining with immunoadsorbed anti-CAP37 antiserum in corneal epithelium obtained from rabbit 10 hr post infection, ×100 (g) Immunohistochemical localization of CAP37 in rabbit eye 15 hr post infection. Strong positive reaction for CAP37 is observed in corneal epithelium as well as in infiltrating PMN in corneal stroma and stromal keratocytes, ×400 (h) Immunohistochemical localization of CAP37 20 hr post infection indicating reduced levels of staining for CAP37 in corneal epithelium. Note continued strong staining for CAP37 in PMN at the base of the epithelial layer, ×400.

CAP37 (Cationic Antimicrobial Protein of $M_r$ 37 kDa) is an inflammatory mediator which plays an important role in host defense and inflammation in the systemic circulation (11-15). PMN-CAP37 (SEQ ID NO:1) is constitutively expressed in the granules of human polymorphonuclear neutrophils (PMNs) and in the α granules of platelets (16-17), and due to its strong antibiotic activity was viewed as part of the oxygen-independent killing mechanism of the PMNs (18-20). The native protein (PMN-CAP37) is particularly potent against the Gram negative bacteria including *Escherichia coli*, *Salmonella typhimurium* and *Pseudomonas aeruginosa* (18-20). Peptides based on the native CAP37 sequence have demonstrated antibiotic activity against the Gram positive bacteria, *Enterococcus faecalis* and *Staphylococcus aureus* (11). In addition to its effects on bacteria, CAP37 has many important functional effects on mammalian cells. CAP37 exerts powerful chemotactic activity for monocytes (13) and regulates endothelial cell functions, such as stimulating protein kinase C (12).

CAP37 proteins and peptides derived therefrom can be used as a topical/oral/intravenous/intravitreal antibiotic for the treatment of ocular bacterial infections in mammals including humans, primates, rabbits, livestock animals and ungulates, for example. CAP37 and CAP37 peptides described herein can also be used to promote healing of corneal wounds and ulcers that may not have an infective component, such as those due to injury by foreign objects or trauma. CAP37 and CAP37 peptides described herein can also be used to treat contact lenses, to sterilize the lenses and inhibit infections caused by bacteria on the lenses. Mammalian corneal transplants can also be stored in media containing CAP37 and/or CAP37 peptides as described herein.

The present invention contemplates these treatments using a CAP37 protein (native, synthetic, or recombinant) such as a CAP37 shown in SEQ ID NO:1, or SEQ ID NO:2. The present invention also contemplates the use of CAP37 peptides including CAP37 peptide 20-44 (SEQ ID NO: 3), CAP37 peptide 23-42 (SEQ ID NO:4), CAP37 peptide 102-122 (SEQ ID NO:5), CAP37 peptide 120-146 (SEQ ID NO:6), and monocysteine derivatives of CAP37 peptide 23-42 and CAP37 peptide 20-44, (including peptides of SEQ ID NO:7 and SEQ ID NO:8) having the formula, for example:

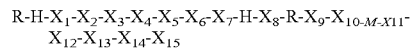

wherein $X_1$ and $X_9$ are phenylalanine and/or tyrosine; $X_2$ and $X_{15}$ are cysteine, serine, and/or threonine; $X_3$ and $X_4$ are glycine and/or alanine; $X_5$-$X_8$, $X_{10}$, $X_{12}$ and $X_{13}$ are alanine, leucine, isoleucine and/or valine; $X_{11}$ is serine and/or threonine; $X_{14}$ is serine, threonine, histidine, arginine or lysine; R is arginine; H is histidine; M is methionine; and with the proviso that one of $X_2$ and $X_{15}$ is cysteine and one of $X_2$ and $X_{15}$ is serine or threonine.

To investigate the biological significance of CAP37 in corneal infection, inflammation and healing, we used a well characterized in vivo rabbit model of *S. aureus* keratitis (21,22). An unexpected and surprising observation was the expression of a CAP37 protein in corneal epithelial cells, stromal keratocytes, ciliary epithelium, related limbus and ciliary vascular endothelium and bulbar conjunctiva. Particularly striking was the extremely strong staining for CAP37 in corneal epithelium (23). The in vivo studies outlined here demonstrate the kinetics of expression of CAP37 in extra-neutrophilic sites including corneal epithelium and stromal keratocytes. These findings were further dissected using in vitro studies in which human corneal epithelial cells and stromal keratocytes were used to determine the mechanism of induction of CAP37 in these cells. Molecular cloning of corneal epithelial-derived CAP37 (EPI-CAP37-SEQ ID NO:2) was undertaken to confirm our immunocytochemical analysis that the corneal epithelial-derived protein was unequivocally CAP37. The results of the present work indicate that CAP37 has far wider ranging effects on the inflammatory process than acting solely as an antibiotic and plays a significant role in the sequence of events involved in leukocyte emigration and epithelial-leukocyte interactions in the inflamed cornea following infection.

Corneal epithelial wound healing has been described as comprising three sequential events: cell migration, cell proliferation and cell adhesion (24-26). We addressed the effect of CAP37 in vitro on these three critical elements of wound healing. Corneal epithelial cell proliferation was assessed using the CyQuant proliferation assay. Cell migration was determined by measuring chemotaxis using the modified Boyden chemotaxis chamber assay. Migration of leukocytes from the vasculature is dependent on the upregulation of adhesion molecules, therefore we measured the effect of CAP37 on upregulation of E-selectin, intercellular adhesion molecule-1 (ICAM-1), vascular cell adhesion molecule-1 (VCAM-1), and platelet endothelial cell adhesion molecule-1 (PECAM-1) on human corneal epithelial cells (HCEC). Since attachment of the newly formed epithelium to the extracellular matrix is essential for completing the healing process we measured adhesion molecules such as β1, β2, β3, β4, αv, α1, α2, α3 and α4 that are capable of binding to fibronectin, laminin and other extracellular matrix proteins (27) contributing to the formation of attachments and adhesion, thereby aiding the healing process.

Corneal Expression of CAP37

Methods

In Vivo Model of *Staphylococcus aureus* Keratitis

A rabbit model of *S. aureus* keratitis was used to determine the localization of CAP37 in the eye in response to infection. The model is well established and the methodology published previously (21-22). Maintenance of animals and all in vivo experimentation was performed according to institutional guidelines and the Association of Research in Vision and Ophthalmology resolution on the use of animals in research. Briefly, New Zealand white rabbits (2.0-3.0 kg) were injected intrastromally with approximately 100 cfu of log phase *S. aureus* (RN6390 a wild-type strain generously provided by Dr. Ambrose Cheung, Rockefeller University, New York, N.Y.) (28). The contralateral eye was injected intrastromally with either phosphate buffered saline (PBS, 0.01 M, pH 7.4 containing 0.15 M NaCl; sham control) or was left undisturbed (absolute control). The rabbit eyes were assessed every 5 hr post infection by slit lamp examination (TOPCON BIOMICROSCOPE SL-5D, Kogaku Kikai K.K., Tokyo, Japan) (21, 22, 29). The course and severity of *S. aureus* keratitis caused by strain RN6390 in these experiments was found to be similar to our previous reports (21, 22, 29). Eyes were enucleated at 5, 10, 15, 20 and 25 hr post infection and processed for histologic analysis by fixing in 10% formalin for 24 hours. Tissue embedding, processing and sectioning was performed according to standard histologic techniques (Dean McGee Eye Institute, Histology Service Facility, Oklahoma City, Okla.).

Cell Culture

Immortalized human corneal epithelial cells (HCEC) provided by Dr. Araki-Sasaki, Suita, Japan were maintained as previously published (30). Briefly, HCEC were cultured in defined keratinocyte serum-free medium (GIBCO BRL, Grand Island, N.Y.) containing 1% penicillin-streptomycin (GIBCO BRL). Human stromal keratocytes were derived from donor corneas (North Florida Lions Eye Bank, Jacksonville Fla.) and cultured in Dulbecco's modified Eagle's medium (DMEM, Mediatech, Herndon, Va.) containing 10% fetal bovine serum (FBS, HYCLONE LABORATORIES, Logan, Utah) and 1% penicillin-streptomycin (GIBCO BRL) according to our previous methods (31). Media changes were made every two to three days, and cells were subcultured (0.25% trypsin-1 mM EDTA at 37° C. for 5 minutes, GIBCO BRL) when they reached 70% confluence at a split ratio of 1:3. For measurement of cell adhesion molecules, the cells were detached using 5 mM EDTA alone (37° C. for 10 min). Cells were transferred to serum free basic medium overnight before the start of each experiment.

Recombinant CAP37

Functionally active recombinant CAP37 (rCAP37) was produced using a RSV-PL4 expression system in human 293 cells (32). The recombinant protein was characterized as to amino acid sequence, SDS polyacrylamide gel electrophoresis and western blots and was shown to be identical to native PMN-derived CAP37. All preparations of rCAP37 comprised <0.1 endotoxin units/pg as determined by the limulus amebocyte lysate assay (QCL 100, WHITTAKER BIOPRODUCTS, Walkersville, Md.) performed exactly according to the manufacturer's instructions.

Immunohistochemistry

The immunohistochemical analysis performed on paraffin-embedded formalin-fixed rabbit eyes was according to previously published methods (13, 33). We used a previously characterized monospecific mouse anti-CAP37 antiserum (13) and the VECTASTAIN™ avidin-biotin-complex (ABC) Elite technique (VECTOR LABORATORIES, Burlingame, Calif.) to detect CAP37. Briefly, 5 µm sections were cut along the optical axis and following the various blocking steps (33) were incubated in the primary antibody (mouse anti-human CAP37 at 1: 1000 dilution in PBS containing 0.1% normal goat serum and 0.1% bovine serum albumin) for 60 min at room temperature. Following three washes in buffer the slides were incubated for 30 minutes in the secondary antibody (biotinylated goat anti-mouse IgG, VECTASTAIN ABC Elite, VECTOR LABORATORIES) and then processed exactly as described in our previous publication (33). In order to determine non-specific staining, negative controls without the primary antibody, normal mouse serum, and immunoadsorbed anti-CAP37 antiserum were incorporated in each experiment. Tissues were viewed under an Olympus BH-2 (Hitschfel Instruments, Inc, Lake Success, N.Y.) microscope and photographs taken using an Olympus C-35AD4 camera.

For immunocytochemical analysis of HCEC and stromal keratocytes in culture, the cells were cultured on coverslips (CORNING COSTAR, Acton, Mass.) placed within 24-well tissue culture plates (CORNING COSTAR) until they reached 70% confluence and immunostained for CAP37 as described above except for the following changes. Cells were fixed in formol-acetone, pH 7.4 for 60 s at 4° C. (13) and were stained using the mouse anti-human CAP37 antiserum (1:500 dilution).

In Vitro Induction of CAP37 in HCEC and Keratocytes

To determine if pro-inflammatory cytokines could induce CAP37 in HCEC and keratocytes we treated these cell cultures with TNF-α (0-10 ng/ml, Boehringer-Mannheim, Indianapolis, Ind.) and IL-1β (0-20 ng/ml, ENDOGEN, Woburn, Mass.) for 0-24 hr and assayed the cells immunocytochemically for the presence of CAP37 protein as described above. Untreated cell cultures were included for each test sample. In addition to protein detection, upregulation of CAP37 mRNA in response to TNF-α and IL-1β was measured by RT-PCR as described below.

RT-PCR

Cultured HCEC were treated with 5 ng/ml TNF-α and 10 ng/ml IL-1β for 0-8 hr at 37° C. Total cellular RNA was isolated from untreated and treated HCEC according to vendor specifications (TRIzol™, Gibco BRL). After reverse-transcription of 5 µg of total RNA by random oligonucelotide priming (hexanucleotide mix, BOEHRINGER-MANNHEIM, GmbH, Germany), the resulting single stranded cDNA was amplified by PCR (PERKIN ELMER 2400 thermocycler, Norwalk, Conn.) using CAP37 specific primers (CAGAATCAAGGCAGGCACTTCTGC (SEQ ID NO:9) and GAGAACACCATCGATCGAGTCTCG (SEQ ID NO:10)) designed for a 597 bp internal fragment of HL60-CAP37 (34). The reaction conditions for reverse transcription were 80 units of RNAse inhibitor (SIGMA), 8 µl of 5× strand buffer, 2 µl of random hexanucleotide mix, 1 mM dNTPs (GIBCO BRL), 10 mM DTT (GIBCO BRL), and 400 units of M-MLV RT (GIBCO BRL) in a total volume of 100 µl. The reaction mix was incubated at 37° C. for 50 min followed by incubation at 70° C. for 15 min. The PCR mix (1.5 mM $MgCl_2$, 0.2 mM dNTPs, 1.26 µM of each primer and 1 unit Taq polymerase, GIBCO BRL) was amplified for 30 cycles. Amplified DNA fragments were separated by electrophoresis on a 1% agarose gel and visualized by exposure to UV after ethidium bromide (0.5 µg/ml) staining. To assess the integrity of the cDNA, primers for human β-actin were used.

Molecular Cloning and Sequencing of HCEC CAP37

The cDNA products from the above RT-PCR were excised from the agarose gel and purified with the GENE CLEAN II KIT (BIO 101, Vista Cailf.) and then cloned using the TA CLONING KIT (INVITROGEN, Carlsbad, Calif.) according to the manufacturer's instructions. Ten white transformants from each treatment were chosen for plasmid DNA isolation and purification (WIZARD PLUS SV miniprep DNA purification system, Promega, Madison Wis.). Plasmids were sequenced in both forward and reverse directions using the T7 and M13 reverse primers from 6 different clones from three independent clonings. The resulting sequences were aligned using Pôle Bio-Informatique Lyonnais, Network Protein sequence @nalysis (35) for DNA and the consensus sequence compared against the HL-60 CAP37 cDNA sequence (34).

Flow Cytometry

Flow cytometry was used to assess the upregulation of ICAM-1 and VCAM-1 on HCEC in response to CAP37 treatment. HCEC were cultured as described above and treated with CAP37 (0-2000 ng/ml) for 0, 2, 6, 24, 48 and 72 hr. A corresponding culture was left untreated at each time point. Following treatment with CAP37, cells were detached with 5 mM EDTA (pH 7.4, Fisher Scientific), washed twice in PBS and fixed with 0.125% paraformaldehyde (J. T. Baker, Phillipsburg, N.J.) overnight at 4° C. The cells were washed in PBS and then incubated in 0.5% normal goat serum and 0.5% BSA in PBS for 30 min to block non-specific binding sites. For determination of ICAM-1 expression, cells were incubated in the primary antibody (FITC-labeled mouse anti-human ICAM-1, BIOSOURCE, Camarillo, Calif.) at $10^6$ cells/10 µl at 4° C. for 1 hr. Cells were washed in PBS and analyzed by flow cytometry (FACSTAR, BECTON DICKINSON, San Jose, Calif.). For detection of VCAM-1 expression, cells were incubated with unlabeled primary antibody (monoclonal mouse anti human VCAM-1, ENDOGEN, Woburn, Mass. at 2 µg/$10^6$ cells) followed by FITC-labeled goat anti-mouse IgG (PHARMINGEN, San Diego, Calif.) at 5 µg/$10^6$ cells and incubated at 4° C. for 30 min. The isotype control for these studies was FITC-labeled mouse isotype $IgG_1$ (PHARMINGEN). The positive control used in these studies was TNF-α (5 ng/ml). At least ten thousand cells were analyzed for each sample.

Statistical Analysis

Data from the adhesion molecule studies are presented as mean±SE. Groups were compared by unpaired student's t-test followed by ANOVA. $P<0.05$ was considered significant.

Results

In Vivo Expression of CAP37 in *S. aureus* Keratitis Model

Immunohistochemical analysis was performed on tissue sections obtained from eyes at 5, 10, 15, 20 and 25 hr post injection of *S. aureus*. The initial detection of CAP37 was made in the limbal epithelium and to a lesser extent in the corneal epithelium at 5 hr (FIG. 1*a*). Staining for CAP37 was not observed in sham-injected eyes at 5 hr post infection (FIG. 1*b*) or at the later time points (not shown). By 10 hr post infection, strong staining for CAP37 was demonstrated in the corneal epithelium (FIG. 1*c*), ciliary epithelium, related limbus and ciliary vascular endothelium (FIG. 1*d*), and bulbar conjunctiva in rabbits injected with *S. aureus*. Staining for CAP37 was not observed in sections stained with normal mouse serum (FIG. 1*e*) or with antiserum immunoadsorbed with CAP37 (FIG. 1*f*). The antibody control in FIGS. 1*e* and 1*f* indicate the specificity of the reaction for CAP37. No PMN or other leukocytic infiltration was observed in the cornea at the 10 hr time point. However, a few PMN were seen in the bulbar conjunctiva and the corneal limbus. The strong staining for CAP37 in the corneal epithelium persisted up to 15 hr (FIG. 1*g*) and began to wane by 20 hr (FIG. 1*h*). Staining for CAP37 in stromal keratocytes was more marked at the 15 hr time point than at the 10 hr time point. An important observation in this in vivo model was that CAP37 induction in vivo was observed before leukocyte infiltration, which in our studies occurred at 15 hr post infection (FIG. 1*g*). Neutrophils were first seen in the stroma at approximately 15 hr post injection of the pathogen, and then began to accumulate at the base of the epithelial layer between 20 and 25 hr post infection (FIG. 1*h*). Obvious stromal edema and severe anterior chamber inflammatory reaction were also readily observed at the later time points. With time, the inflammatory reaction became more severe; clumps of bacteria were evident within the stroma but the levels of CAP37 in the corneal epithelium and stromal keratocytes diminished. It is important to note that PMN continued to stain for CAP37 throughout all the time points (FIG. 1*h*), even though epithelial CAP37 was reduced or could no longer be detected.

In Vitro Expression of CAP37 in Human Corneal Epithelial Cells and Keratocytes

Figure 2:
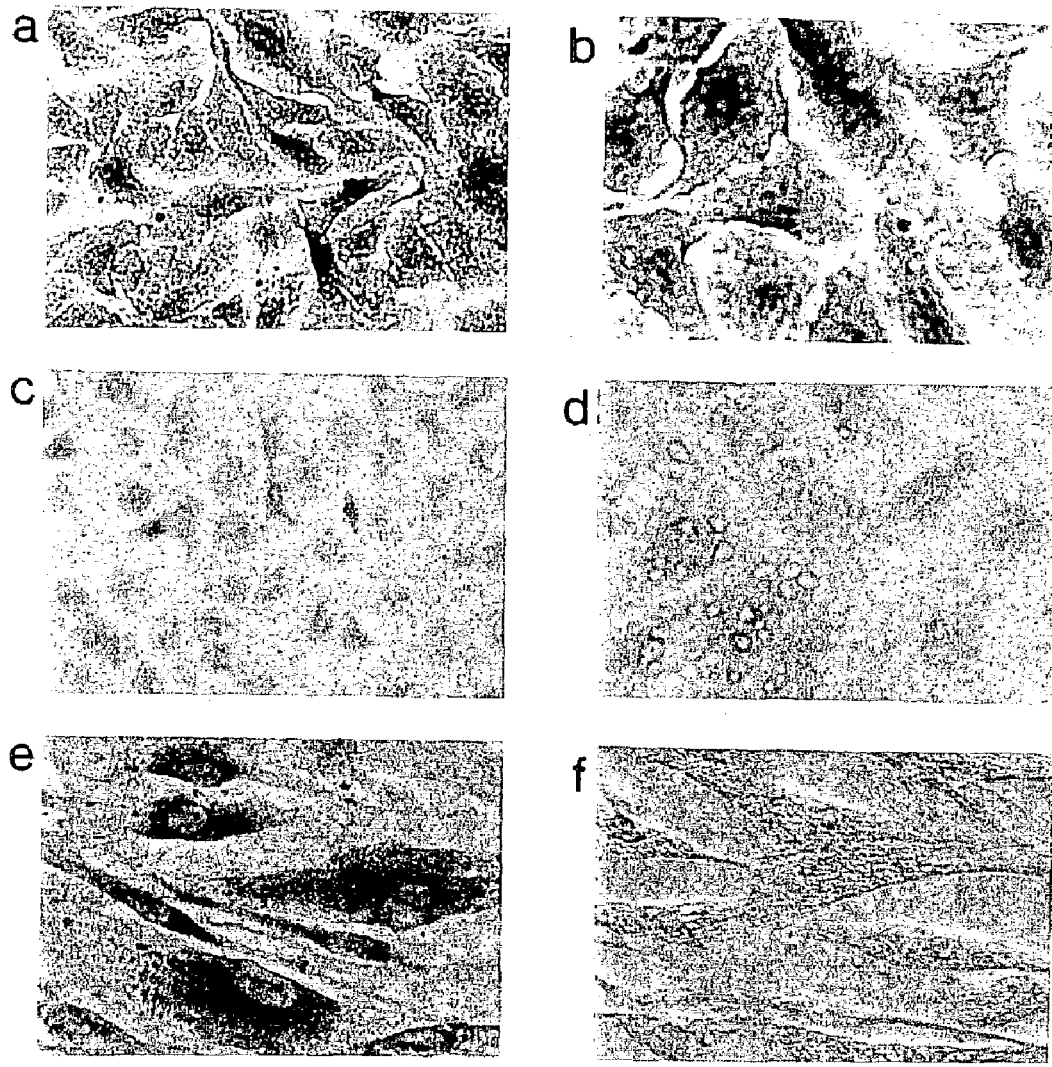
FIG. 2. In vitro induction of CAP37 in human corneal epithelial cells (HCEC) and stromal keratocytes. (a) Representative figure indicating immunohistochemical detection of CAP37 protein using mouse anti-CAP37 antiserum and the Vectastain ABC-peroxidase staining technique on HCEC treated with tumor necrosis factor-α (TNF-α 5 ng/ml) for 24 hr, ×200 (b) Induction of CAP37 in HCEC in response to Interleukin-1β (IL-1β 10 ng/ml) treatment for 24 hr. ×400 (c) Staining using mouse anti-CAP37 antiserum on untreated HCEC indicating absence of staining for CAP37, ×100 (d) Antibody control using immunoadsorbed anti-CAP37 antiserum on HCEC treated with IL-1β (10 ng/ml) for 24 hr, ×200 (e) Induction of CAP37 in stromal keratocytes in response to TNF-α (10 ng/ml for 24 hr) as detected immunohistochemically using mouse-anti-CAP37 antiserum, ×400 (f) Immunoadsorbed anti-CAP37 antiserum control indicating absence of CAP37 in stromal keratocytes treated with TNF-α (10 ng/ml for 24 hr), ×400.

Since CAP37 was detected in the corneal epithelium and stromal keratocytes in vivo in response to the intrastromal Gram-positive infection but was not present in normal, uninfected eyes, the possibility that CAP37 was induced in response to inflammatory mediators and/or cytokines generated as part of the host's defense response to the infection was studied. Two proinflammatory cytokines, TNF-α and IL-1β, are known to be present during the acute stages of a wide range of inflammatory situations (36-39), and have been implicated in gene expression of other chemoattractants such as IL-8 (40-41). Using immunocytochemistry and RT-PCR we explored the possibility that they might regulate CAP37 expression in HCEC and keratocytes. The immunocytochemical data presented in FIG. 2 demonstrate that CAP37 protein is induced in HCEC in response to TNF-α (FIG. 2*a*) and IL-1β (FIG. 2*b*). Detection of CAP37 protein was observed as early as 60 min in the TNF-α treated cells and appeared maximum at 24 hr. Expression of CAP37 in response to IL-1β was observed at a later time point (4 hr) and like TNF-α appeared to have its maximum effect at 24 hr. There was no constitutive expression of CAP37 protein in untreated HCEC (FIG. 2*c*). Antibody controls using immunoadsorbed anti-CAP37 antiserum showed no staining, indicating the specificity of this reaction (FIG. 2*d*). Stromal keratocytes treated with TNF-α (FIG. 2*e*) and IL-1β (not shown) showed the induction of CAP37 protein. Once again there was no constitutive expression of CAP37 in these cells as indicated by a lack of staining with the anti-CAP37 antiserum in the untreated cell cultures (not shown). The specificity of this reaction was demonstrated by the lack of staining with the immunoabsorbed antibody control (FIG. 2*f*).

Figure 3:
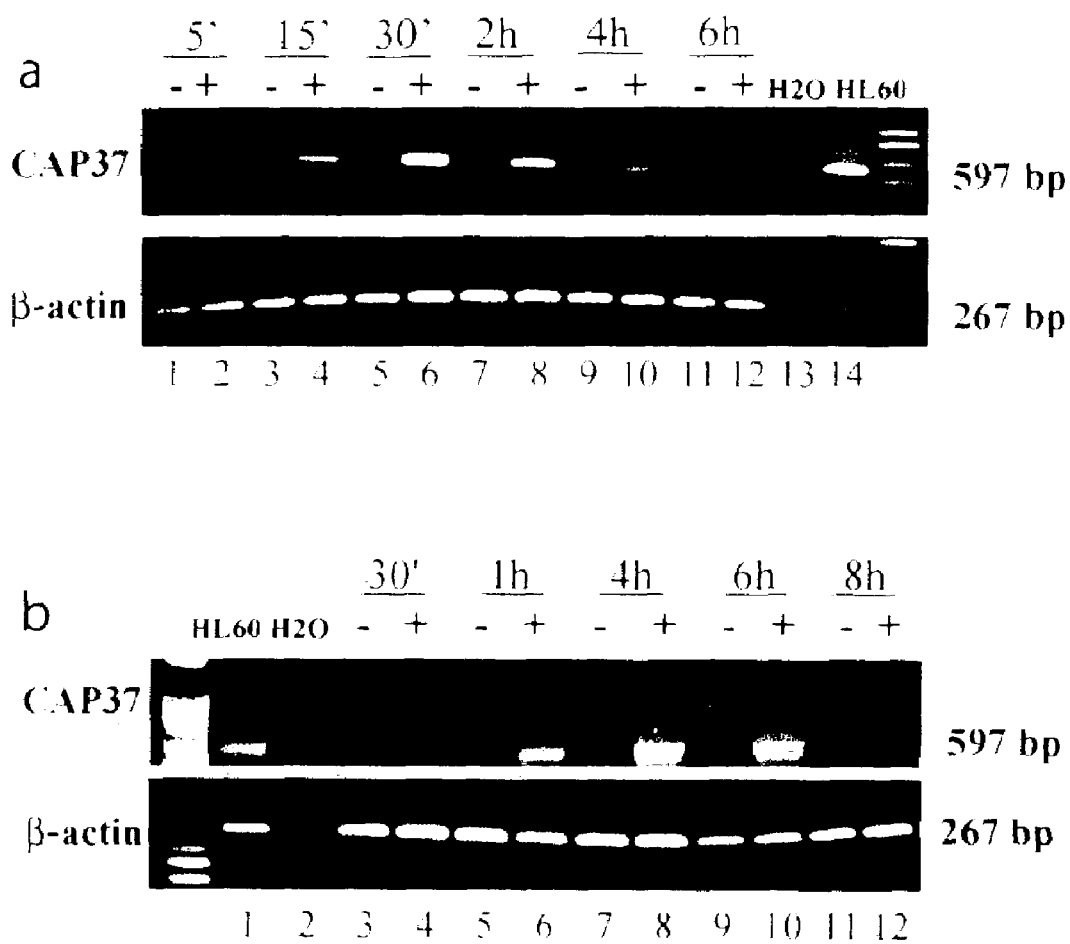
FIG. 3. Kinetic study demonstrating the effect of proinflammatory cytokines on steady state levels of CAP37 mRNA in corneal epithelial cells. (a) HCEC were treated (+) with TNF-α (5 ng/ml) for 5 min, 15 min, 30 min, 2 hr, 4 hr and 6 hr and CAP37 mRNA expression (upper panel, 597 bp) determined by RT-PCR. Untreated (−) HCEC controls are included for each time point. Lane 13 is a negative-water control. Lane 14 is the positive HL-60 control. (b) HCEC were treated with IL-1β (10 ng/ml) for 0.5, 1, 4, 6, and 8 hr and CAP37 mRNA expression (upper panel 597 bp) determined by RT-PCR. Untreated (−) controls are included for each incubation point. Lane 1 is the positive HL-60 control and lane 2, the negative-water control. The lower panel in both indicates cDNA integrity as assessed with the β-actin primer (267 bp). Molecular markers are present in unmarked lanes in both panels.

We corroborated the immunocytochemical data above using RT-PCR. Human corneal epithelial cells treated with TNF-α (FIG. 3*a*) and IL-1β (FIG. 3*b*) showed a time-dependent expression of CAP37 mRNA. Untreated HCEC do not express CAP37 mRNA. However, on treatment with the proinflammatory cytokine, TNF-α, HCEC express CAP37 mRNA as early as 15 minutes. These levels are maximum between 30 min and 2 hr, and reduced by 4 hr. IL-1β also induced CAP37 mRNA in HCEC. However as demonstrated in FIG. 3*b*, the initial expression of CAP37 mRNA is delayed and is not detected until 1 hr post stimulation. Furthermore, the effect is more sustained than with TNF-α, as the message can be detected even at 6 hr. These findings corroborate our immunocytochemical data in which TNF-α induced protein at an earlier time point and that the more intense staining of CAP37 was obtained in response to IL-1β.

Molecular Cloning of Human Corneal Epithelial Cell CAP37 (EPI-CAP37)

To determine whether EPI-CAP37 (SEQ ID NO:2) was similar to PMN-CAP37 (SEQ ID NO:1) we undertook the cloning of HCEC-CAP37. Total cellular RNA was isolated from HCEC treated with TNF-α for 2 hr and cDNA synthesis performed according to the methodology described above. RT-PCR was used to amplify the CAP37 gene from HCEC using the pair of oligonucleotide primers as described in the methods and based on a previously published cDNA sequence of CAP37 (34). EPI-CAP37 has the same sequence as residues 20-218 of PMN-CAP37 (SEQ ID NO: 1) except for amino acid residue at position 113 of EPI-CAP37 (SEQ ID NO:2), wherein a histidine residue consistently replaced the arginine residue found at the corresponding position in PMN-CAP37 (i.e., residue 132 of SEQ ID NO:1).

Upregulation of ICAM-1 on Cultured HCEC

Figure 4:
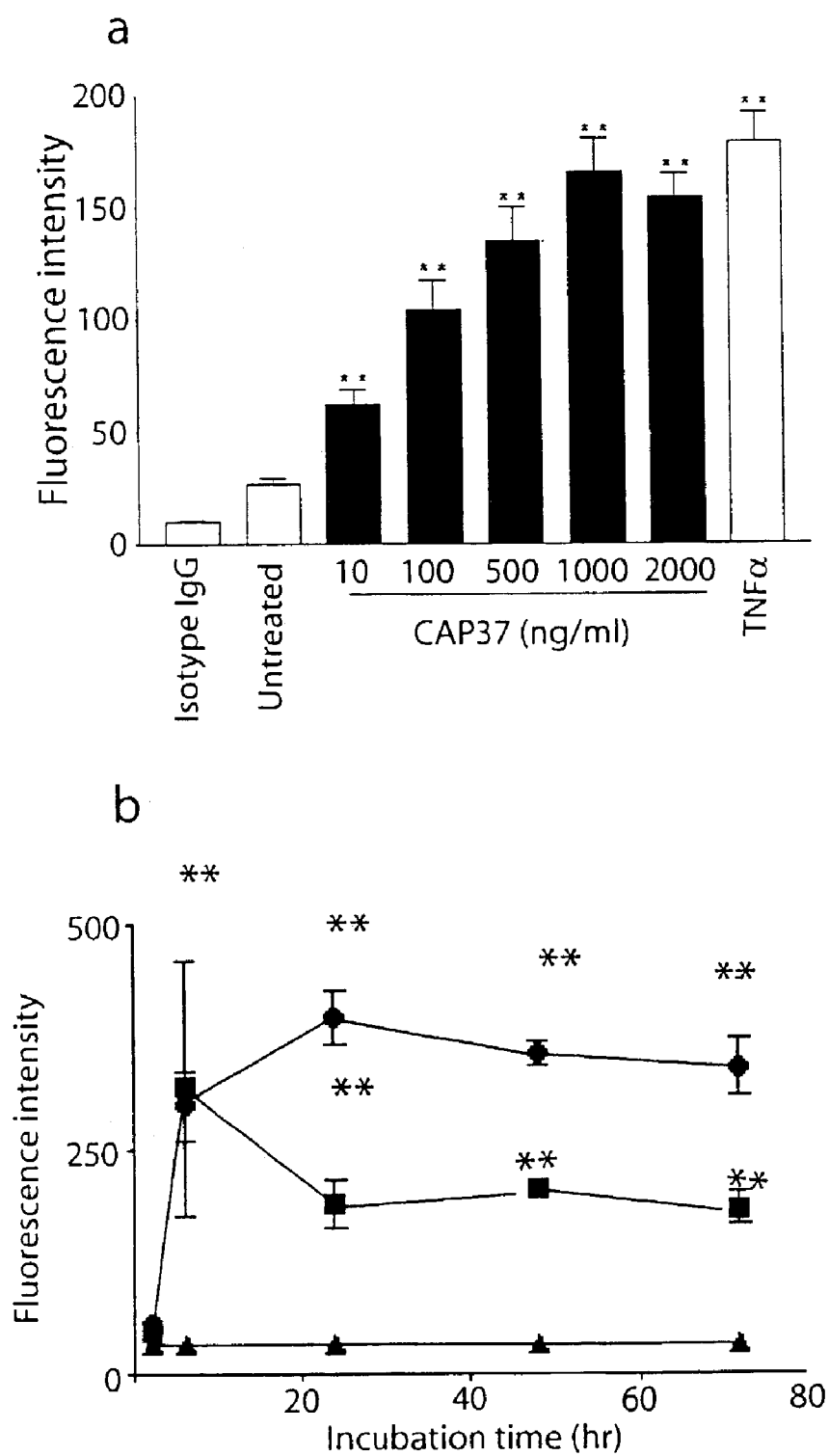
FIG. 4. Upregulation of intercellular adhesion molecule-1 (ICAM-1) on human corneal epithelial cells in response to CAP37. (a) Dose response effect of CAP37 on expression of ICAM-1 on cultured HCEC. Cells were treated with CAP37 (0-2000 ng/ml) for 6 hr and stained with FITC-labeled mouse anti-human ICAM-1 and fluorescence intensity measured by flow cytometry. Controls included the isotype $IgG_1$ antibody and TNFα (5 ng/ml), which served as the positive control. Values are mean±SE of results obtained from 9 independent experiments.  P<0.01 compared to untreated control. (b) Kinetic response of CAP37-mediated expression of ICAM-1 in HCEC. Cells were treated with 1000 ng/ml of CAP37 (circles) at 2, 6, 24, 48, & 72 hr and ICAM-1 expression analyzed by flow cytometry. TNF-α at 5 ng/ml (squares) was used as the positive control. Untreated controls are indicated by triangles. Values are mean±SE of results obtained from three independent experiments.  P<0.01 compared to untreated control.

In vitro studies were undertaken to investigate the effect of CAP37 on the upregulation of ICAM-1, on HCEC. Cells were treated with CAP37 (0-2000 ng/ml) for 0-72 hr and levels of ICAM-1 measured using flow cytometry. ICAM-1 was upregulated by CAP37 in a dose-dependent fashion, with maximum upregulation obtained with 1000-2000 ng/ml of CAP37 (FIG. 4a). These levels were comparable to those obtained with the positive control TNF-α (5 ng/ml). Lower, yet significant levels of ICAM-1 were obtained with CAP37 at concentrations between 10 and 500 ng/ml. Kinetic studies (FIG. 4b) indicated that HCEC did not constitutively express ICAM-1 and that no upregulation of ICAM-1 could be detected by flow cytometry at the early time point of 2 hr. However by 6 hr, significant upregulation of ICAM-1 was observed. The levels declined by 24 hr, but were still above the untreated levels.

As noted previously, extravasation of leukocytes from the circulation into tissue sites is an integral feature of the host response to injury and inflammation (42). By virtue of their ability to engulf and destroy bacteria, eliminate toxins and secrete numerous soluble mediators, leukocytes are capable of restricting and limiting the spread of infection. In the acute stages of most infections, the predominant cell type is the PMN (42, 43). This observation held true in our in vivo rabbit model of S. aureus keratitis, where the primary leukocyte observed in the initial 25 hr period following infection was the PMN. The rabbit bacterial keratitis model indicated the expected expression of CAP37 in the granules of migrating PMN. However, a surprising and unexpected observation was the expression of CAP37 in corneal epithelial cells, stromal keratocytes, ciliary epithelium, related limbus and ciliary vascular endothelium and bulbar conjunctiva. Particularly striking was the extremely strong staining for CAP37 in corneal epithelium at 10 hr post infection. The induction of CAP37 in the cornea occurred prior to the emigration of PMN, which in this model occurred approximately 15 hr post infection. The path of migration of PMN appeared to be from ciliary and limbal vessels through the stroma to the basal aspects of the epithelial layer, where large numbers of PMN were seen to accumulate.

Clearly, as indicated by the present results, extra-neutrophilic CAP37 is induced in response to infection or an inflammatory stimulus, since sham-injected animals do not show staining for CAP37. These are significant findings, since the extra-neutrophilic localization of CAP37 in ocular tissue in response to infection has not been reported previously. Our data indicate that the source of CAP37 in the corneal epithelium is endogenous during the early stages of infection. This is based on our unequivocal observations that corneal CAP37 is seen in the absence of and prior to PMN extravasation. Thus the staining observed in the epithelium could not be due to exogenously released CAP37 from PMN. Our in vitro studies depicted in FIGS. 2 and 3 support the concept that CAP37 can be induced in any ocular infection in which TNF-α and IL-1β are generated.

Our in vitro studies show that the pro-inflammatory mediators TNF-α and IL-1β regulate CAP37 expression in corneal epithelial cells and stromal keratocytes in a time- and dose-dependent fashion. Untreated cells did not display CAP37 message or protein, indicating that it is not constitutively expressed in either of these cells. This is the first demonstration of the expression of a monocyte chemoattractant in HCEC in response to cytokines. The induction of monocyte chemotactic protein-1 (MCP-1), RANTES (44), and GROα (45), members of the C-C chemokine family with chemotactic effects on monocytes has been demonstrated in stromal keratocytes but not in HCEC. On the other hand, expression of C-X-C chemoattractants such as IL-8 with potent effect on PMN migration can be induced in HCEC (40) and stromal keratocytes (31). These studies demonstrate a novel localization of the inflammatory mediator CAP37 and indicate that these new properties contribute to its role in host defense in ocular inflammation.

Modulation of Corneal Epithelial Cell Functions by CAP37

Methods

Cell Culture

Immortalized human corneal epithelial cells (HCECs,) provided by K. Araki-Sasaki, (Suita, Japan) (30) were grown and maintained in defined keratinocyte-serum free media (GIBCO BRL, Grand Island, N.Y.) containing 1% penicillin-streptomycin (GIBCO BRL) as described previously (31). Media changes were made every two to three days and cells were subcultured (0.25% trypsin-1 mM EDTA at 37° C. for 5 minutes, GIBCO BRL) when they reached 70% confluence at a split ratio of 1:3.

Recombinant CAP37

Functionally active recombinant CAP37 (rCAP37) was produced and characterized as described above.

Cell Proliferation

Human corneal epithelial cells were seeded onto 48 well tissue culture plates ($7.5 \times 10^3$ cells/well, FALCON, Franklin Lakes, N.J.) and cultured as described above.

Cultures were changed to growth factor-free basic medium overnight and treated with various concentrations of CAP37 (0-2000 ng/ml) for 48-72 hrs. Recombinant human Epidermal Growth Factor (EGF 50 ng/ml, BECTON DICKINSON, Bedford, Mass.) and recombinant human Hepatocyte Growth Factor/Scatter Factor (HGF/SF 20 ng/ml, BECTON DICKINSON) were used as positive controls and growth factor-free basic medium as negative control. The medium was aspirated and new medium with CAP37 or growth factors were added to the cultures every 24 hr. The CyQUANT Cell Proliferation Assay Kit (MOLECULAR PROBES, Eugene, Oreg.) was used to quantify cell proliferation exactly according to the manufacturer's specifications. Briefly, cells were frozen, thawed, and lysed with the addition of the lysis buffer containing the green fluorescent dye, CyQUANT GR which binds to nucleic acids and the fluorescence levels read on fluorescent micro plate reader (fmax MOLECULAR DEVICES, Sunnyvale, Calif.) with filters for 485 nm excitation and 538 nm emission.

Chemotaxis Assay

Human corneal epithelial cells were cultured in basic medium overnight, detached using trypsin-EDTA as described above and resuspended at a final concentration of $8 \times 10^5$ cells/ml. Chemotaxis assays were performed using the modified Boyden chamber assay described previously (13). Briefly, 200 (µl of cell suspension was added to the upper chamber and chemoattractants including recombinant CAP37 (10-2000 ng/ml) and the positive control recombinant human Platelet Derived Growth Factor-BB (PDGF-BB, 10 ng/ml, Collaborative Biomedical Products, Bedford Mass.) in 0.1% BSA (endotoxin-low-Sigma, St. Louis) in Geys' Buffer (GIBCO) were added to the lower chamber. The chambers were separated by an 8.0 µm pore membrane (13 mm polyvinylpyrrolidone-free, Whatman, Clifton, N.J.). Membranes were pre-coated with 50 µg/ml collagen type I rat tail (Collaborative Biomedical Products) in 0.02N acetic acid at room temperature for 1 hr and then air dried. Membranes were re-hydrated in basic cell culture medium immediately prior to commencement of each experiment. The negative control in these experiments was 0.1% BSA in Geys' buffer. The chambers were incubated in a humidified atmosphere (37° C., 5% $CO_2$) for 4 hr, the filters were removed, stained with DIFF-QUICK (Dade Behring, Düdingen, Switzerland) and mounted with Permount (FISHER SCIENTIFIC, Pittsburgh, Pa.). The filters were viewed under oil immersion (×400 magnification, BH-2, Olympus, Lake Success, N.Y.) and the total numbers of cells migrated through to the underside of the filter were counted in five different fields on each slide. Triplicates were set up for each experimental point.

To assess whether CAP37 had chemokinetic properties, various concentrations of CAP37 (0, 10, 100 and 1000 ng/ml) were added to the upper chamber as well as to the lower chamber (0, 10, 100, 500, 1000 ng/ml) and a checkerboard assay performed according to the methodology of Zigmond and Hirsch (46).

To determine the specific interaction of CAP37 with HCEC, we used a previously characterized polyvalent, monospecific rabbit antiserum to CAP37 (12) to inhibit the chemotactic activity of CAP37. CAP37 was incubated with heat inactivated (56° C. for 30 min) rabbit antiserum at concentrations of 1: 10, 1:50, and 1:100 and chemotaxis assays performed as outlined above using 500 ng/ml ($1.3 \times 10^{-8}$ M) rCAP37. Controls included heat-inactivated antiserum alone, CAP37 alone, PDGF alone and PDGF plus antiserum.

Flow Cytometry

Flow cytometry was used to assess the upregulation of PECAM-1 (CD31), and the integrin molecules β1 (CD29), β2 (CD18), β3 (CD61), β4 (CD104), α1 (CD49a), α2 (CD49b), α3 (CD49c), α4 (CD 49d), and αv (CD51). Human corneal epithelial cells were cultured as above and treated with CAP37 (0-2000 ng/ml) for 0-72 hr. A corresponding culture was left untreated at each time point. Following treatment with CAP37, cells were detached with 0.25% trypsin in 1 mM EDTA (pH 7.4, FISHER SCIENTIFIC, Pittsburgh, Pa.), washed twice in PBS and fixed with 0.125% paraformaldehyde (J. T. BAKER, Phillipsburg, N.J.) overnight at 4° C. The cells were washed in PBS and then incubated in 0.5% normal goat serum and 0.5% bovine serum albumin (BSA) in PBS for 30 min to block non-specific binding sites. Cells were incubated in the primary antibody (at concentrations described below) at 4° C. for 1 hr followed by the secondary antibody (FITC-goat anti-mouse IgG, PHARMINGEN, San Diego, Calif.) at 0.5 µg/$10^6$ cells and incubated at 4° C. for 30 min. The isotype control for these studies was FITC-labeled mouse isotype $IgG_1$ (PHARMINGEN). The cells were analyzed by flow cytometry (FACS Calibur, BECTON DICKINSON, San Jose, Calif.). At least ten thousand cells were analyzed for each sample.

Antibodies

The primary antibodies and the concentrations used in the flow cytometry experiments are as follows: mouse anti-human PECAM-1 (CD31) monoclonal antibody clone HEC7 (0.5 µg/$10^6$ cells, ENDOGEN, Woburn, Mass.), mouse anti-human very late antigen 1α (VLA-1α, or CD49a) monoclonal antibody clone SR84 (0.5 µg/$10^6$ cells, PHARMINGEN), mouse anti-human VLA-$\alpha_2$ (CD49b) monoclonal antibody clone AK-7 (0.125 µg/$10^6$ cells, PHARMINGEN), mouse anti-human α3 (CD49c) monoclonal antibody clone C3II.1 (0.125 µg/$10^6$ cells, PHARMINGEN), mouse anti-human VLA-4 (α4) monoclonal antibody clone 2B4 (1 µg/$10^6$ cells, R & D systems, Minneapolis, Minn.), mouse anti human α5 (CD49e) monoclonal antibody clone VC5 (0.125 µg/$10^6$ cells, PHARMINGEN), mouse anti-human $\beta_1$ (CD29) monoclonal antibody MAR4 (2 µg/$10^6$ cells, PHARMINGEN), mouse anti human $\beta_2$ integrin (CD18) monoclonal antibody clone 6.7 (0.5 µg/$10^6$ cells, PHARMINGEN), mouse anti human $\alpha_v\beta_3$ (CD51/CD61) monoclonal antibody clone 23C6 (0.5 µg/$10^6$ cells, PHARMINGEN), and mouse anti human integrin $\beta_4$ (CD104) monoclonal antibody clone 450-11A (1.0 µg/$10^6$ cells, PHARMINGEN). A purified mouse $IgG_1$ κ monoclonal immunoglobulin isotype standard (clone MOPC-31C) was used as the isotype matched control in the flow cytometry experiments.

RT-PCR

Cultured HCEC were treated with CAP37 (1 µg/ml) for 0-24 hr at 37° C. Total cellular RNA was isolated from untreated and treated HCEC according to vendor specifications (TRIzol™, GIBCO BRL). After reverse-transcription of 5 µg of total RNA by SuperScrip™ II RT (GIBCOBRL) the resulting single stranded cDNA was amplified by PCR (BIOMETRA TGRADIENT, Göttingen, Germany) using specific primers for ICAM-1 ((GTCCCCCTCAAAAGT-CATCC (SEQ ID NO:11) and AACCCCATTCAGCGT-CACGT (SEQ ID NO: 12)); VCAM-1 ((AGTGGTGGC-CTCGTGAATGG (SEQ ID NO:13) and CTGTGTCTCCTGTCTCCGCT (SEQ ID NO:14)); PECAM-1 ((TTGCAGCACAATGTCCTCTC (SEQ ID NO: 15) and AGCACAGTGGCAACTACACG (SEQ ID NO:16)); E-selectin ((AGAAGAAGCTTGCCCTATGC (SEQ ID NO:17) and AGGCTGGAATAGGAGCACTCCA (SEQ ID NO:18)); and β-actin ((TACCTCATGAAGATC-CTCA (SEQ ID NO: 19) and TTCGTGGATGCCACAG-GAC (SEQ ID NO:20))) synthesized by the Molecular Biology Resource Facility, University of Oklahoma Health Sciences Center. The thermocycler conditions for ICAM-1 and VCAM-1 were 95° C. for 5 min initially, with 30 cycles at 95° C. for 1 min, 58° C. for 45 sec, 72° C. for 1 min followed by a final extension at 72° C. for 7 min. The conditions for E-selectin were 95° C. for 5 min initially, with 30 cycles at 94° C. for 1 min, 58° C. for 1 min, 72° C. for 1 min followed by a final extension at 72° C. for 5 min. The conditions for PECAM-1 were 95° C. for 5 min initially, with 30 cycles at 95° C. for 45 sec, 60° C. for 1 min, 72° C. for 1 min followed by a final extension at 72° C. for 5 min.

Amplified DNA fragments were separated by electrophoresis on a 1% agarose gel and visualized by exposure to UV after ethidium bromide (0.5 µg/ml) staining. Expected sizes for ICAM-1, VCAM-1, PECAM-1, E-selectin and β-actin were 943 bp, 700 bp, 677 bp, 315 bp and 267 bp, respectively. To assess the integrity of the cDNA, primers for human β-actin were used.

Statistical Analysis

Data from proliferation and chemotaxis and adhesion molecule studies are presented as mean±SE. Groups were compared by unpaired student's t-test followed by ANOVA. $P<0.05$ was considered significant.

display a certain level of chemokinesis particularly at higher concentrations (46). The data obtained clearly demonstrate that there is an increase in numbers of cells migrating across the filter when increasing concentrations of CAP37 are present in the lower chamber, but absent from the upper chamber i.e. standard chemotaxis assay (Table I, row 1). The addition of CAP37 to the upper chamber resulted in a reduction of the chemotactic gradient across the membrane, with corresponding reduction in levels of migration. The values on the diagonal in Table I represent chambers that were set up with equal concentrations of CAP37 across the membrane and clearly indicate that the levels of migration are not significantly greater than background. The values in Table I are represented as total numbers of cells migrated rather than percent of control to indicate the absolute values of cells migrating to the underside of the filter.

TABLE I

| Concentration of CAP37 above the filter (ng/ml) | Number of cells migrated |  |  |  |  |
|---|---|---|---|---|---|
|  | Concentration of CAP37 below the filter (ng/ml) |  |  |  |  |
|  | 0 | 10 | 100 | 500 | 1000 |
| 0 | 24.06 ± 2.80 | 28.56 ± 7.64 | 39.82 ± 6.20 | 68.89 ± 7.70*** | 67.34 ± 8.42 *** |
| 10 | ND | 27.63 ± 3.03 | 39.80 ± 6.93 | 52.40 ± 15.76*** | 62.73 ± 9.66*** |
| 100 | ND | ND | 36.63 ± 6.48 | ND | 48.57 ± 15.58*** |
| 1000 | ND | ND | 28.08 ± 2.76 | ND | 38.13 ± 6.07 |

Determination of chemokinetic properties of CAP37 by the checkerboard assay for HCEC. CAP37 has some chemokinetic activity at the higher concentrations, but it contributes little to the overall chemotactic effect on HCEC.

Results

Proliferation of HCEC in Response to CAP37

Figure 5:
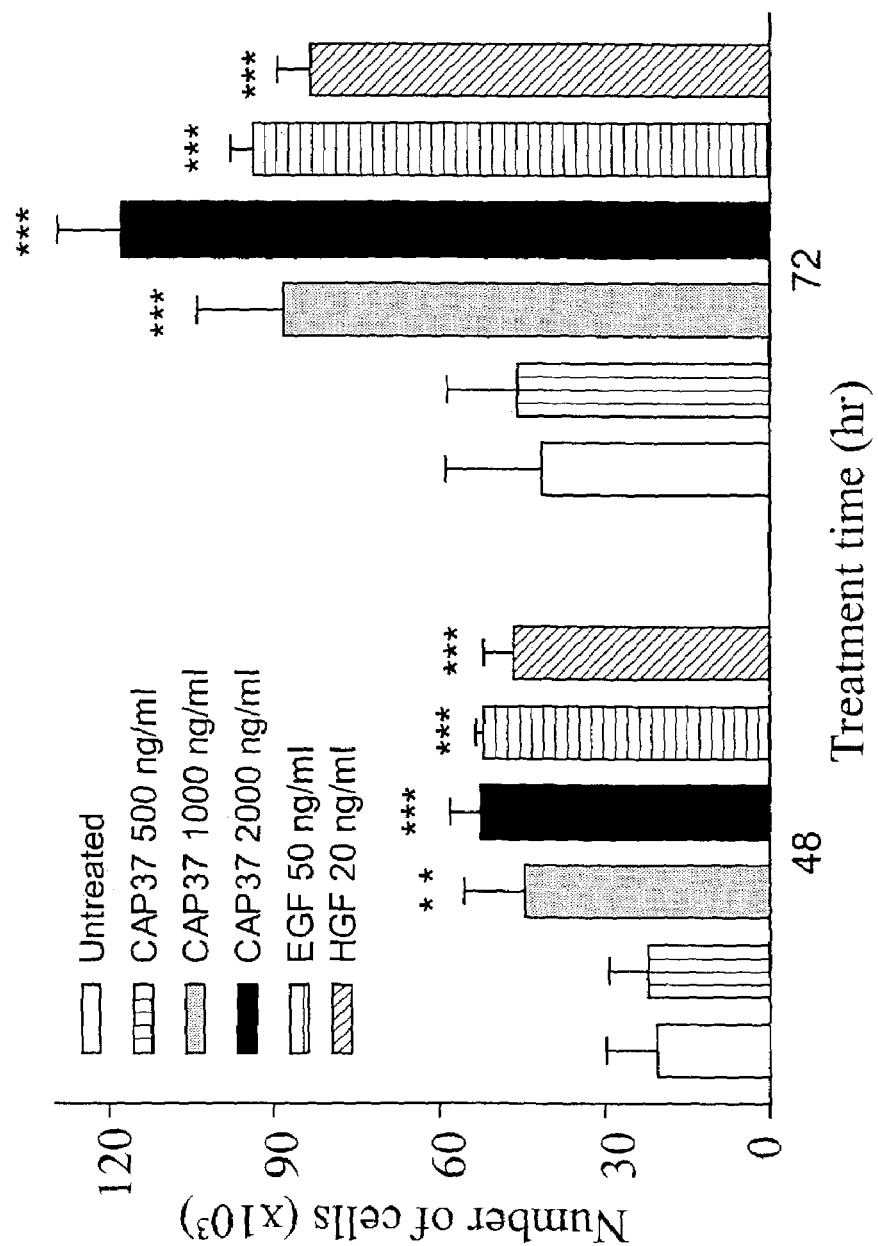
FIG. 5. Proliferation of human corneal epithelial cells (HCEC) in response to CAP37 using the CyQuant assay. CAP37 significantly (*** P<0.001) affects the proliferation of HCEC in a time and dose dependent fashion. Levels of proliferation obtained with 1000 and 2000 ng/ml of CAP37 were comparable to those obtained with the two positive controls epidermal growth factor (EGF) and hepatocyte growth factor (HGF). Data are ±SE of 4 independent experiments performed in triplicate.

CAP37 significantly affects the proliferation of HCEC (FIG. 5). This response is both dose- and time-dependent. At 48 hours post treatment with CAP37, there was a significant increase in proliferation over basal levels observed in culture medium alone. Levels of proliferation obtained with 1000-2000 ng/ml ($2.7$-$5.4 \times 10^{-8}$ M) of CAP37 were comparable to those obtained with the two positive controls, EGF and HGF. HCEC continued to proliferate with time and an approximately two- to three-fold increase in cell numbers was obtained at 72 hr post treatment with 1000 ng/ml and 2000 ng/ml of CAP37 respectively. The levels obtained with EGF and HGF were similar to those obtained with 1000 ng/ml of CAP37.

Migration of HCEC in Response to CAP37

Figure 6:
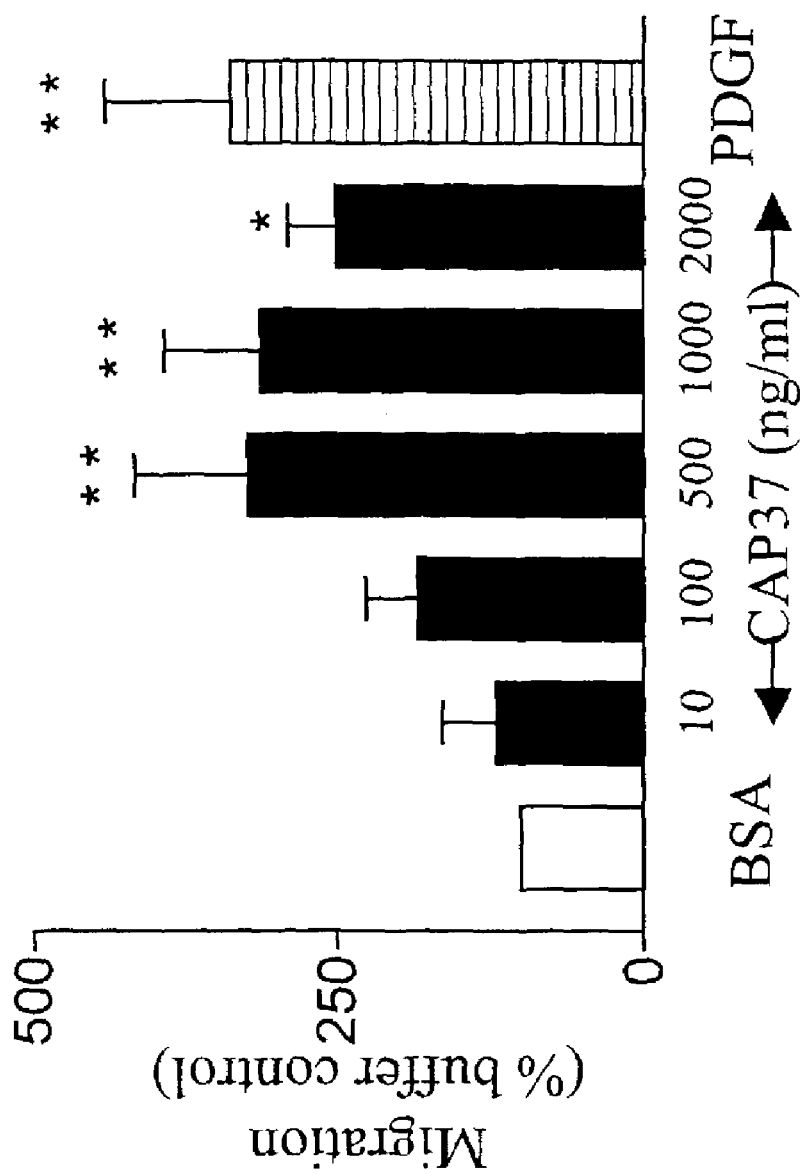
FIG. 6. Migration of HCEC in response to CAP37 using the Boyden chemotaxis chamber assay. CAP37 is maximally chemotactic in the range of 500-1000 ng/ml and was reduced but still measurable at 2000 ng/ml. The levels of migration were comparable to those obtained with the positive control, platelet derived growth factor (PDGF). Data are mean± of 3 independent experiments performed in triplicate. * P<0.05 and ** P<0.01 compared to the untreated buffer control.
Figure 7:
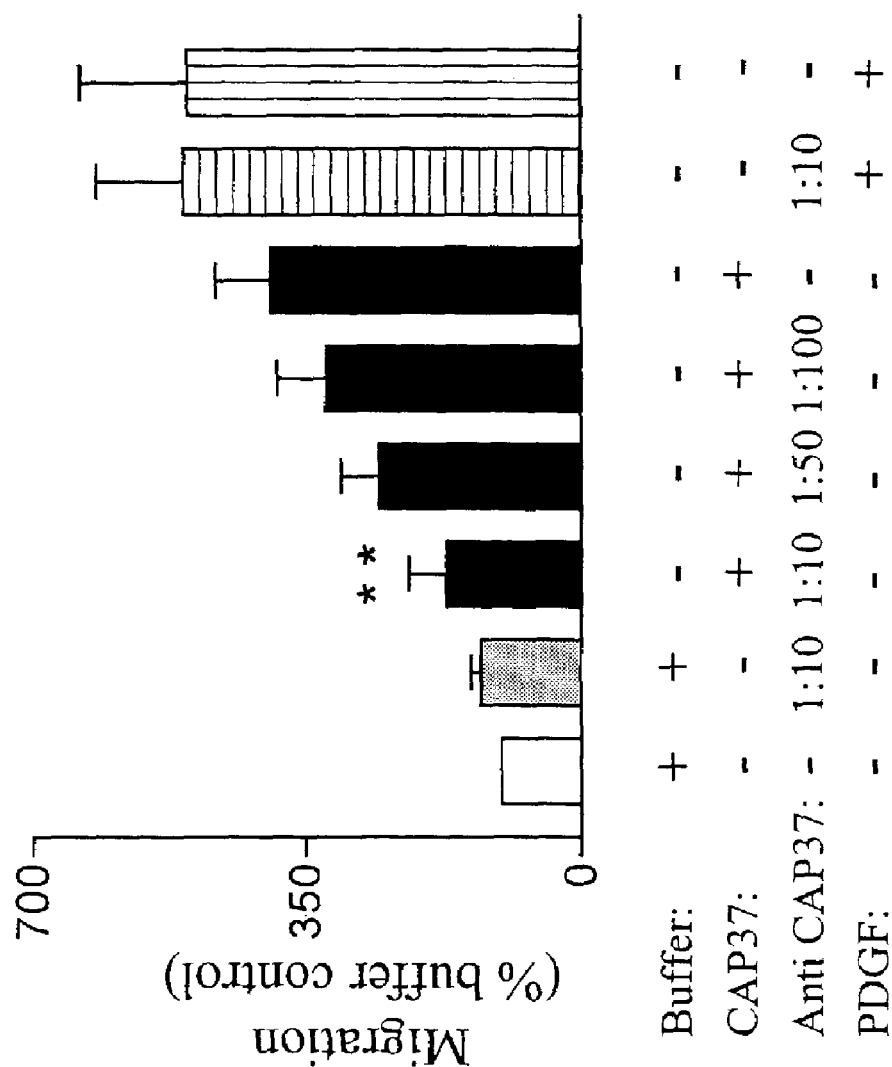
FIG. 7. Inhibition of HCEC migration in response to CAP37 using a specific antiserum to CAP37. Dose response inhibition of the chemotactic response, with significant inhibition (**P:<0.01) obtained with the antibody at 1:10 dilution. No inhibition obtained on the chemotactic activity of PDGF for HCEC.

We investigated whether CAP37 was chemotactic for HCEC using the modified Boyden chemotaxis technique. Data shown in FIG. 6 indicate that CAP37 is a strong chemoattractant for HCEC. It was maximally chemotactic in the range of 500 ng/ml to 1000 ng/ml and was reduced but still measurably active at 2000 ng/ml. The levels of migration in response to CAP37 were comparable to those obtained with the positive control, PDGF. The dose response obtained with CAP37 shows the typical bell-shaped curve indicative of a chemoattractant. However, an important issue that requires clarification when determining movement of cells in response to a mediator is whether this migration is due to directed movement (chemotaxis) as opposed to merely accelerated random motion (chemokinesis). The checkerboard assay (46) has been traditionally employed to distinguish chemotaxis from chemokinesis. Our experiments demonstrate that the effect of CAP37 on HCEC is predominantly chemotactic (Table I). Most chemoattractants To demonstrate the specificity of this chemotactic response, an antibody previously shown to be specific for CAP37 was used to inhibit the migration of cells in response to CAP37. FIG. 7 indicates a dose response inhibition of the chemotactic response, with significant inhibition ($p<0.01$) obtained with the antibody at 1:10 dilution. As predicted, the antibody did not have an inhibitory effect on the chemotactic activity of PDGF for HCEC.

Effect of CAP37 on adhesion molecules on HCEC

Figure 8:
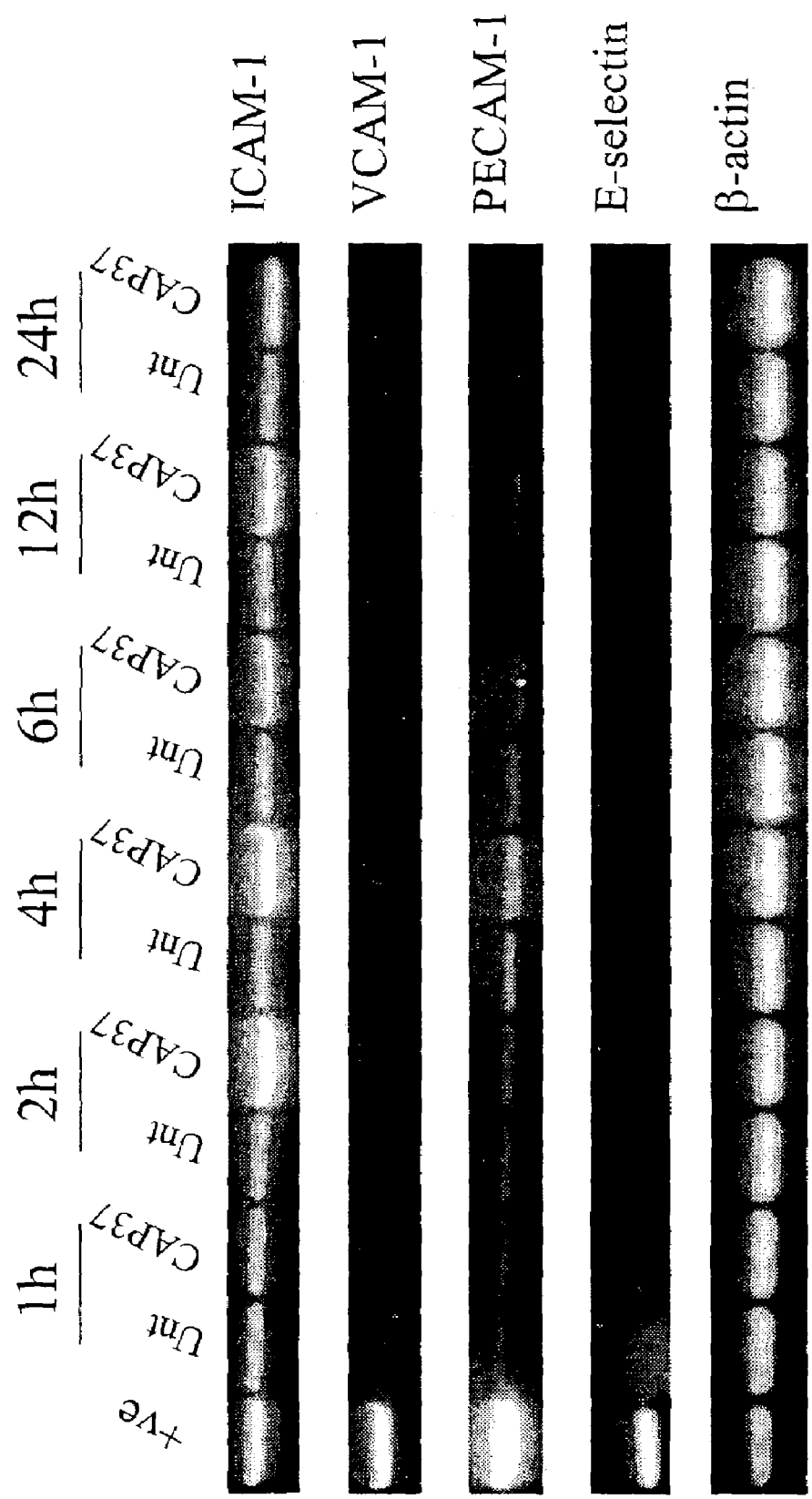
FIG. 8. RT-PCR analysis of HCEC for adhesion molecules ICAM-1, VCAM-1, PECAM-1 and E-selectin. ICAM-1 is constitutively expressed and was significantly upregulated in the presence of CAP37. PECAM-1 was also upregulated by CAP37. There was no upregulation of VCAM-1 and E-selectin mRNA expression in response to CAP37 treatment. +Ve=positive TNFα-treated control; Unt=untreated; CAP37=CAP37 treated for 1, 2, 4, 6, 12, and 24 hr.

RT-PCR was performed using primers specific for ICAM-1, VCAM-1, PECAM-1 and E-selectin. Treatment of HCEC with CAP37 indicates a clear upregulation of ICAM-1 message beginning at 2 hr and lasting through 24 hr (FIG. 8). Maximum expression of ICAM-1 message was seen between 2 and 4 hr. PECAM-1 was also upregulated by CAP37. Unlike the upregulation of ICAM-1 message, upregulation of PECAM-1 message was transient. It was detected at 2 hr after stimulation, maximum at 4 hr and could not detected after 6 hr. HCEC did not show increase in mRNA expression of VCAM-1 and E-selectin in response to CAP37 treatment.

Figure 9:
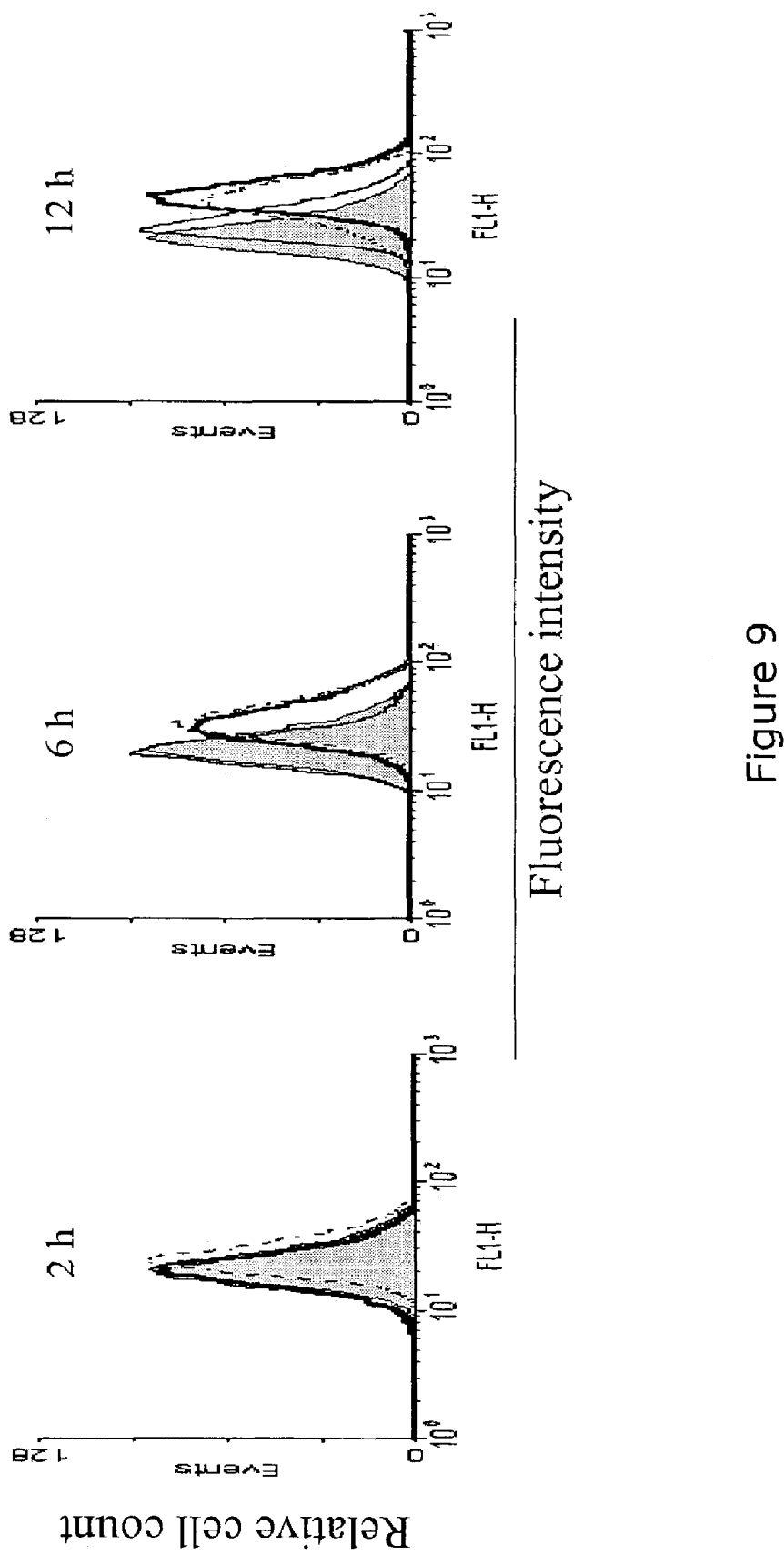
FIG. 9. Kinetic expression of PECAM-1 in response to CAP37 measured by flow cytometry. Grey shaded area=isotype control, light line=untreated control, dashed line=TNF-α control, dark line=CAP37 at 1 μg/ml. Upregulation is significant between 6 and 12 hr.

The expression of PECAM-1 in response to CAP37 treatment was further confirmed using flow cytometry (FIG. 9). Significant protein expression was observed on HCEC at 6 hr, was maintained through 12 hr and waned by 24 hr, corroborating our findings in FIG. 8. The kinetics of this response to CAP37 appeared to follow that of TNF-α up to 12 hr. Thereafter the effect of TNF-α was more sustained, lasting until 24 hr (not shown).

Figure 10:
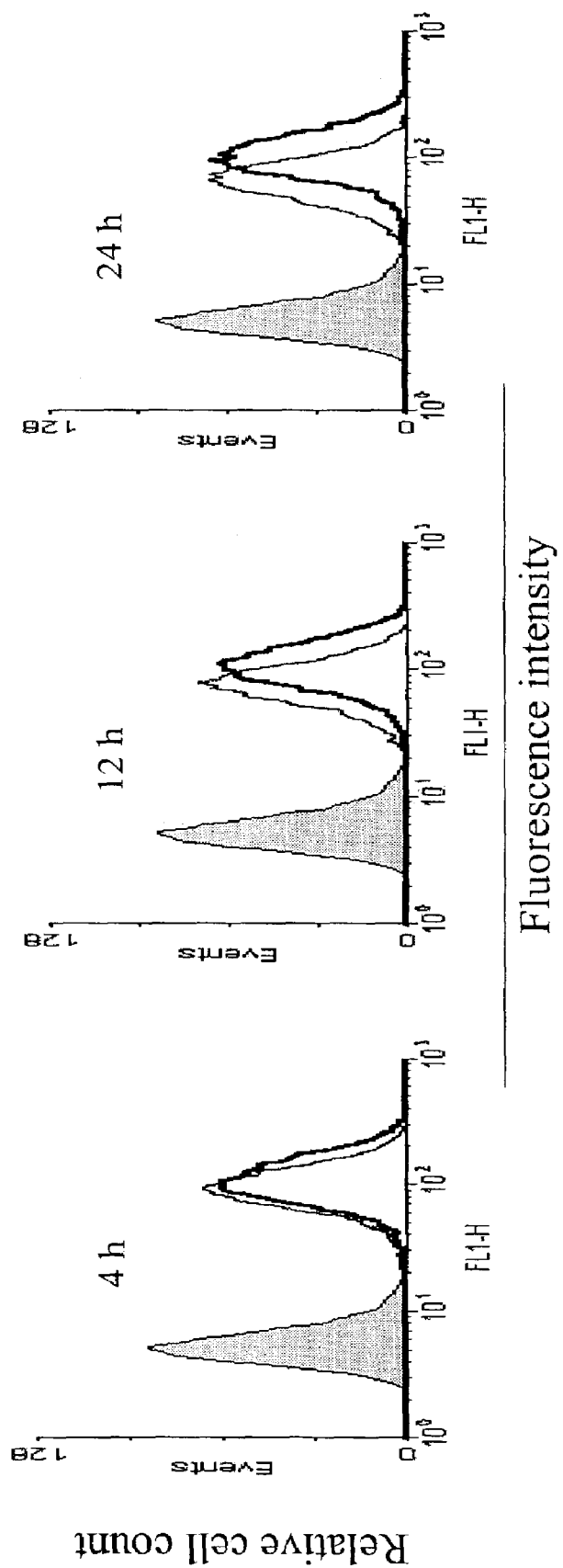
FIG. 10. Kinetic expression of CD49c integrin molecule in response to CAP37 measured by flow cytometry. Initial upregulation of CD49c at 4 hr with sustained protein expression through 24 hr. Grey shaded area=isotype control, light line=untreated control, dark solid line=CAP37 treatment.
Figure 11:
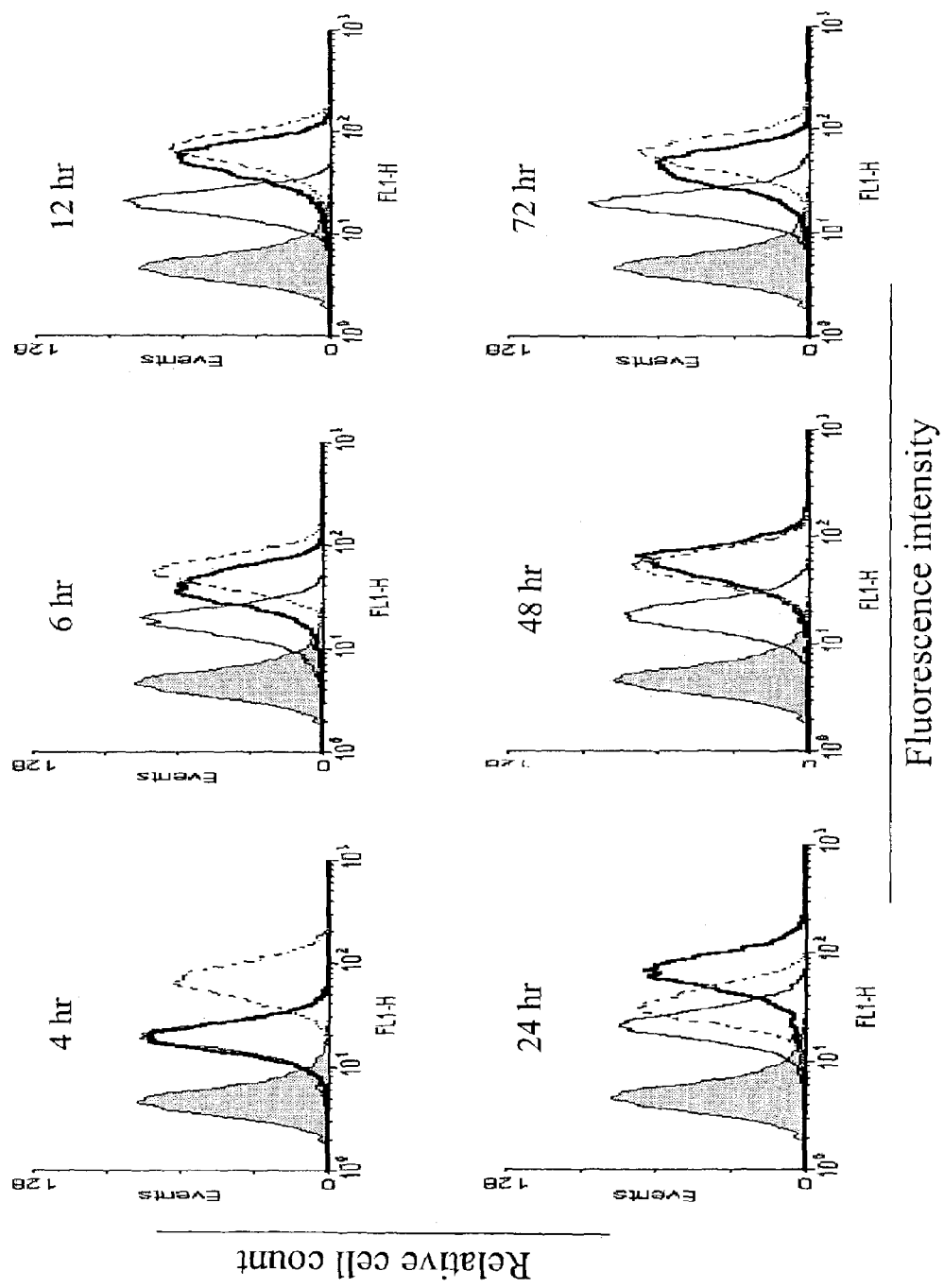
FIG. 11. Kinetic expression of CD29 integrin molecule in response to CAP37 as measured by flow cytometry. Grey shaded area=isotype control, light line=untreated control, dashed line=TNF-α control, dark solid line=CAP37 treatment.

Upregulation of α1, α2, α3, α4, αv and β1, β2, β3, β4 integrins in response to CAP37 was also assessed using flow cytometry. Table II summarizes the data obtained from these analyses. Of the 8 integrin molecules analyzed only two showed significant upregulation. CD49c (α3) was initially upregulated at 4 hr, and the level of protein expression was sustained through 24 hr (FIG. 10). CD49c protein levels on HCEC at 48 and 72 hr returned back to constitutive levels (not shown). There was high contitutive expression of CD49c, as indicated by strong staining on untreated HCEC. The other integrin molecule to be upregulated by CAP37 was CD29 (β1). The upregulation is clearly significant by 6 hr, increases to maximum levels between 12 and 48 hr, and although reduced at 72 hr is still significantly elevated above background constitutive levels (FIG. 11). The flow cytometry analysis indicates a low level of constitutive expression of CD29 which remains constant throughout all time points in this experiment. TNF-α was used as the positive control in these experiments.

TABLE II

| Integrin molecule | Effect of CAP37 |
| --- | --- |
| α1 (CD49a; VLA-α1) | Constitutive expression-no upregulation |
| α2 (CD49b; VLA-α2) | Constitutive expression-no upregulation |
| α3 (CD49c) | High constitutive expression-significant up regulation |
| α4 (CD49d) | Low constitutive expression-no upregulation |
| β1 (CD29) | Constitutive expression-significant upregulation |
| β2 (CD18) | No constitutive expression-no upregulation |
| β4 (CD104) | Constitutive expression-no upregulation |
| αv β3 (CD51/CD61) | Low constitutive expression-no upregulation |

Effect of CAP37 on integrin molecules on HCEC

As indicated by the results, the presence of the novel inflammatory molecule CAP37 has been identified in the eye. The in vitro evidence presented indicates its expression in HCEC and stromal keratocytes in response to inflammatory cytokines such as TNF-α and IL-1β. The results show that CAP37 modulates corneal epithelial cell functions including proliferation, migration and upregulation of adhesion molecules important in epithelial-extracellular matrix interactions. In addition to upregulation of adhesion molecules important in epithelial-extracellular matrix interactions, CAP37 also regulates the expression of adhesion molecules of the immunoglobulin superfamily important in leukocyte-epithelial interactions. Specifically, CAP37 upregulated the adhesion molecules ICAM-1 and PECAM-1. CAP37 modulates infections in the eye through its ability to act as an antibiotic, elicit leukocyte recruitment and affect corneal epithelial cells functions, thereby regulating corneal inflammation and healing.

Utility

The present invention contemplates the use of a native, synthetic, or recombinant CAP37, or peptide portions thereof, or derivatives thereof, as described herein, to treat various conditions of the eye including infections. The invention further contemplates the use of a native, synthetic, or recombinant CAP37, or peptide portions thereof, or derivatives thereof, in the treatment of corneal ulcers and wounds. The invention also contemplates the use of a native, synthetic, or recombinant CAP37, or peptide portions or derivatives thereof, as a disinfectant for cleaning or sterilization of contact lenses and as a storage solution for preventing contact lenses from becoming contaminated with bacteria while in contact lens storage cases. The invention also contemplates coating contact lenses with a native, synthetic, or recombinant CAP37, or an antibiotic peptide portions or derivatives thereof (and contact lenses thus coated), to inhibit, prevent or treat infections, bacterial keratitis and/or the growth of biofilms on or by contact lenses. The invention also contemplates a method for storage of mammalian corneal tissue or transplants in media containing a native, synthetic, or recombinant CAP37, or peptide portions or derivatives thereof, or at bactericidal concentrations for aseptic transportation and storage.

CAP37 peptides which can be used in the present invention are functional (antibiotic) and immunomodulatory peptides of CAP37 peptides of CAP37 or derivatives thereof and include, but are not limited to, peptide 20-44, peptide 23-42, peptide 102-122, peptide 120-146, and monocysteine derivatives of peptides 20-44 and 23-42 as described in U.S. Pat. No. 6,107,460 which is hereby expressly incorporated by reference herein in its entirety and as referred to elsewhere herein.

More particularly the invention includes, but is not limited to:

1. Use of a native, synthetic, or recombinant CAP37, or peptides thereof, and/or derivatives thereof, as described herein, as an ocular antibiotic treatment, for conjunctivitis or bacterial keratitis, particularly in those cases due to *Pseudomonas aeruginosa* and *Staphylococcus aureus*.
2. Use of a native, synthetic, or recombinant CAP37, or peptides thereof, and/or derivatives thereof, as described herein, as a cleaning and sterilization procedure for storing contact lenses in storage cases. Since *Pseudomonas aeruginosa* is the most common causative agent, contact lenses could be stored in a bactericidal solution of a native, synthetic, or recombinant CAP37, or peptides thereof, and/or derivatives thereof as described herein. This would be an important mechanism to prevent or inhibit ocular infections before they are initiated.
3. Extended wear contact lenses could be manufactured with a surface coating of a native, synthetic, or recombinant CAP37, or bactericidal peptides thereof, and/or derivatives thereof, as described herein, as a preventive method to prevent or inhibit infections from occurring or biofilms from forming.
4. Human corneal transplants could be stored in media containing bactericidal quantities of a native, synthetic, or recombinant CAP37, or peptides thereof, and/or derivatives thereof, as described herein, during transportation and storage.
5. A native, synthetic, or recombinant CAP37, or peptides thereof, and/or derivatives thereof, as described herein, could be used in treating ulcers and wounds of the cornea to promote healing.
6. Use of a native, synthetic, or recombinant CAP37, or bactericidal peptides thereof, and/or derivatives thereof, as described herein, to treat serious bacterial infections which occur post-operatively. For example, endophthalmitis, including post-operative endophthalmitis due to coagulase negative *Staphylococcus*, is a major problem. Infection of the conjunctival filtering bleb created by glaucoma surgery, known as "blebitis", due most commonly to *Staphylococcus aureus, Streptococcus* and *Hemophilus* are further targets for treatment with a native, synthetic, or recombinant CAP37, or peptides thereof, and/or derivatives thereof, as described herein.

The use of a native, synthetic, or recombinant CAP37, or peptides thereof, and/or derivatives thereof, described herein, as antibiotics is advantageous over other available therapies since its mode of action is different from traditional antibiotics. Therefore the chances of antibiotic resistant organisms arising as a result of this therapy are far less than with traditional antibiotics. Since CAP37 is a naturally occurring protein or peptide, the chances of allergic reactions and toxicity are less. It has activity with a relatively narrow spectrum, but is active against both *Pseudomonas* and *Staphylococcus*, the two most common causative organisms of bacterial keratitis. Further, a native, synthetic, or recombinant CAP37, or peptides thereof, and/or derivatives thereof, are generally bactericidal rather than bacteriostatic.

A native, synthetic, or recombinant CAP37, or peptides thereof, and/or derivatives thereof, as described herein, are active against the two most common causative organisms, but have limited activity against a number of other Gram negative and Gram positive bacteria, therefore, treatment using them would not be overly toxic to normal flora. The CAP37 peptides in particular are small, easily synthesized, and can be delivered in required concentrations topically.

In one treatment protocol, the proteins or peptides described herein are provided at a concentration of 200 µg/ml in a saline or "natural tears" solution, but may be at a concentration from about 10 µg/drop to 1000 µg/drop (50 µl/drop). Drops may be administered to a subject's eye, for example, every 15 minutes to 1 hour for the first 2-3 days of treatment, followed by dosing every 4 hours for 14 more days. The proteins or peptides described herein could also be applied to the eye as an ointment. The CAP37 proteins or peptides can be applied by intravitreal injection for treatment of endophthalmitis in a manner well known to those of ordinary skill in the art.

The following U.S. patents are hereby expressly incorporated herein by reference in their entirety: U.S. Pat. Nos. 5,607,916; 5,650,392; 5,627,262; 5,877,151; 6,071,879; 6,107,460; 5,458,874; and 5,484,885. References cited herein are also expressly incorporated by reference herein in their entireties.

All references, articles and patents cited herein are hereby incorporated herein in their entirety by reference.

While the invention is described herein in connection with certain embodiments so that aspects thereof may be more fully understood and appreciated, it is not intended that the invention be limited to these particular embodiments. On the contrary, it is intended that all alternatives, modifications and equivalents are included within the scope of the invention as defined by the appended claims. Thus the examples described below, which include preferred embodiments, will serve to illustrate the practice of this invention, it being understood that the particulars shown are by way of example and for purposes of illustrative discussion of preferred embodiments of the present invention only and are presented in the cause of providing what is believed to be the most useful and readily understood description of procedures as well as of the principles and conceptual aspects of the invention. Changes may be made in the formulation of the various compositions described herein or in the steps or the sequence of steps of the methods described herein without departing from the spirit and scope of the invention as described and claimed herein.

REFERENCES

1. Baum J. Infections of the eye. *Clin. Infect. Dis.* 1995; 21:479-488.
2. Gritz D C, Whitcher J P. Topical issues in the treatment of bacterial keratitis. *Int. Ophthalmol. Clin.* 1998;38:107-114.
3. Brennan N A, Chantal Coles M L. Extended wear in perspective. *Ophthalmol. Vis. Sci.* 1997; 74:609-623.
4. Levartovsky S, Rosenwasser G, Goodman D. Bacterial keratitis following laser in situ keratomileusis. *Ophthalmology* 2001;108:321-325
5. Neumann M, Sjostrand J. Central microbial keratitis in a Swedish city population. A three-year prospective study in Gothenburg. *Acta. Ophthalmologica.* 1993;71:160-164.
6. Fleisig S M J, Efron N, Pier G B. Extended contact lens wear enhances *Pseudomonas aeruginosa* adherence to human corneal epithelium. *Invest. Ophthalmol. Vis. Sci.* 1992; 33:2908-2916.
7. O'Callaghan R J, Callegan M C, Moreau J M, Green L C, Foster T J, Hartford O M, Engel L S, Hill J M. Specific roles of alpha-toxin and beta-toxin during *Staphylococcus aureus* corneal infection. *Infect. Immun.* 1997;65:1571-1578.
8. Streilein J W, Stein-Streilein J. Does innate immune privilege exist? *J. Leukoc. Biol.* 2000;67:479-487.
9. Streilein J W. Immune regulation and the eye: a dangerous compromise. *FASEB J.* 1987; 1:199-208.
10. Rocha G, Deschenes J, Rowsey J J. The immunology of corneal graft rejection. *Crit. Rev. Immun.* 1998;18:305-325.
11. Pereira H A, Erdem I, Pohl J, Spitznagel J K. Synthetic bactericidal peptide based on CAP37: a 37-kDa human neutrophil granule-associated cationic antimicrobial protein chemotactic for monocytes. *Proc. Natl. Acad. Sci (USA).* 1993;90:4733-4737.
12. Pereira H A, Moore P, Grammas P. CAP37, a neutrophil granule-derived protein stimulates protein kinase C activity in endothelial cells. *J. Leukoc. Biol.* 1996;60:415-422.
13. Pereira H A, Shafer W M, Pohl J, Martin L E, Spitznagel J K. CAP37, a human neutrophil-derived chemotactic factor with monocyte specific activity. *J. Clin. Invest.* 1990; 85:1468-1476.
14. Pereira H A. CAP37, a neutrophil-derived multifunctional inflammatory mediator. *J. Leukoc. Biol.* 1995;57: 805-812.
15. Pereira H A, Spitznagel J K, Pohl J, Wilson D E, Morgan J, Palings I, Larrick J W. CAP37, a 37 kD human neutrophil granule cationic protein shares homology with inflammatory proteinases. *Life Sci.* 1990;46:189-196.
16. Pereira H A, Spitznagel J K, Winton E F, Shafer W M, Martin L E, Guzman G S, Pohl J, Scott R W, Marra M N, Kinkade J M Jr. The ontogeny of a 57 kD cationic antimicrobial protein of human polymorphonuclear leukocytes: Localization to a novel granule population. *Blood* 76:1990;825-834.
17. Flodgaard H, Ostergaard E, Bayne S, Svendsen A, Thomsen J, Engels M, Wollmer A. Covalent structure of two novel neutrophile leukocyte-derived proteins of porcine and human origin. Neutrophile elastase homologues with strong monocyte and fibroblast chemotactic activities. *Eur. J. Biochem.* 1991;197:535-547.
18. Shafer W M, Martin L E, Spitznagel J K. Cationic antimicrobial proteins isolated from human neutrophil granulocytes in the presence of diisopropyl fluorophosphates. *Infect. Immun.* 1984;45:29-35.
19. Spitznagel J K, Pereira H A. Antibiotic proteins of human neutrophils: Interaction with the surface of Salmonella. In: Cabello F, Hormaeche C, eds. *The Biology of Salmonella.* N.Y.: Plenum Press. 1993:149-158
20. Spitznagel J K. Antibiotic proteins of human neutrophils. *J. Clin. Invest.* 1990;86: 1381-1386.
21. Callegan M C, Hobden J A, Hill J M, Insler M S, O'Callaghan R J. Topical antibiotic therapy for the treatment of experimental *Staphylococcus aureus* keratitis. *Invest. Ophthalmol. Vis. Sci.* 1992;33:3017-3023.

22. Callegan M C, Engel L S, Hill J M, O'Callaghan R J. Corneal virulence of *Staphylococcus aureus*: Roles of alpha-toxin and protein A in pathogenesis. *Infect. Immun.* 1994;62:2478-2482.
23. Ruan X, Chodosh J, Callegan M C, Booth M C, Lee T D, Kumar P, Gilmore M S, Pereira H A. Corneal expression of the inflammatory mediator CAP37. *Invest. Ophthalmol. Vis. Sci.* 2002; 43:1414-1421.
24. Lu L, Reinach P S, Kao W W-Y. Corneal epithelial wound healing. *Exp. Biol. Med.* 2001; 226:653-664.
25. Wilson S E, Mohan R R, Mohan R R, Ambrosio R, Jr, Hong J W, Lee J S. The corneal wound healing response: Cytokine-mediated interaction of the epithelium, stroma, and inflammatory cells. *Prog. Ret. Eye Res.* 2001; 20:625-637.
26. Dua H A, Gomes J A P, Singh A. Corneal epithelial wound healing. *Brit. J. Ophthalmol.* 1994; 78:401-408.
27. PäällysahoT, Tervo T, Virtanen I, Tervo K. Integrins in the normal and healing corneal epithelium. *Acta Ophthalmol.* 1992; 70:22-25.
28. Cheung A L, Eberhardt K J, Chung E, Yeaman M R, Sullam P M, Ramos M, Bayer A S. Diminished virulence of a sar⁻ lagr⁻ mutant of *Staphylococcus aureus* in the rabbit model of endocarditis. *J. Clin. Invest.* 1994;94:1815-1822.
29. Hobden J A, Engel L S, Hill J M, Callegan M C, O'Callaghan R J. Prednisolone acetate or prednisolone phosphate concurrently administered with ciprofloxacin for the therapy of experimental *Pseudomonas aeruginosa* keratitis. *Curr. Eye Res.* 1993;12:469-473.
30. Araki-Sasaki K, Ohashi Y, Sasabe T, Hayashi K, Watanabe H, Tano Y, Handa H. An SV-40 immortalized human corneal epithelial cell line and its characterization. *Invest. Ophthalmol. Vis. Sci.* 1995;36:614-621.
31. Chodosh J, Astley R A, Butler M G, Kennedy R C. Adenovirus keratitis: A role for interleukin-8. *Invest. Ophthalmol Vis. Sci.* 2000;41:783-789.
32. Pereira H A, Ruan X, Kumar P. Activation of microglia: A neuroinflammatory role for CAP37. GLIA 2003;41:64-72.
33. Pereira H A, Kumar P, Grammas P. Expression of CAP37, a novel inflammatory mediator in Alzheimer's disease. *Neurobiol. Aging.* 1996; 17:753-759.
34. Morgan J G, Sukiennicki T, Pereira H A, Spitznagel J K, Guerra M E, Larrick J W. Cloning of the cDNA for the serine protease homolog CAP37/azurocidin, a microbicidal and chemotactic protein from human granulocytes. *J. Immunol.* 1991; 147:3210-3214.
35. Corpet F. Multiple sequence alignment with hierarchical clustering. *Nucl. Acids Res.* 1988; 16:10881-10890.
36. Sotozono C, He J, Matsumoto Y, Kita M, Imanishi J, Kinoshita S. Cytokine expression in the alkali-burned cornea. *Curr. Eye Res.* 1997;16:670-676.
37. Nakamura Y, Sotozono C, Kinoshita S. Inflammatory cytokines in normal human tears. *Curr. Eye Res.* 1998; 17:673-676.
38. Hu M, Dutt J, Arrunategui-Correa V, Baltatzis S, Foster C S. Cytokine mRNA in BALB/c mouse corneas infected with herpes simplex virus. *Eye* 1999;13:309-313.
39. Carr D J, Campbell I L. Transgenic expression of interleukin-6 in the central nervous system confers protection against acute herpes simplex virus type-1 infection. *J. Neurovirol.* 1999;5:449-457.
40. Elner V M, Strieter R M, Pavilack M A, Elner S G, Remick D G, Danforth J M, Kunkel S L. Human corneal interleukin-8: IL-1 and TNF-induced gene expression and secretion. *Am. J. Pathol.* 1991;139:977-988.
41. Cubitt C L, Tang Q, Monteiro C A, Lausch R N, Oakes J E. IL-8 gene expression in cultures of human corneal epithelial cells and keratocytes. *Invest. Opthalmol. Vis. Sci.* 1993;34:3199-3206.
42. Hurley J V. *Acute Inflammation*. 2$^{nd}$ ed. Edinburgh: Churchill Livingstone. 1983:109-117.
43. Sloop G D, Moreau J M, Conerly L L, Dajcs J J, O'Callaghan R J. Acute inflammation of the eyelid and cornea in *Staphylococcus* keratitis in the rabbit. *Invest. Ophthalmol. Vis. Sci.* 1999;40:385-391.
44. Tran M T, Tellaetxe-Isusi M, Elner V, Strieter R M, Lausch R N, Oakes J E. Proinflammatory cytokines induce RANTES and MCP-1 synthesis in human corneal keratocytes but not in corneal epithelial cells. (–chemokine synthesis in corneal cells. *Invest. Ophthalmol. Vis. Sci.* 1996;37:987-996.
45. Cubitt C L, Lausch R N, Oakes, J E. Differential induction of GRO (gene expression in human corneal epithelial cells and keratocytes exposed to proinflammatory cytokines. *Invest. Ophthalmol. Vis. Sci.* 1997;38: 1149-1158.
46. Zigmond S, Hirsch J G. Leukocyte locomotion and chemotaxis. New methods for evaluation, and demonstration of a cell-derived chemotactic factor. *J. Exp. Med.* 1973; 137:387-410.

---

What is claimed is:

1. A method of treating an infection in an eye of a mammal comprising:
providing a therapeutically-effective amount of a peptide consisting of the sequence SEQ ID NO:6, SEQ ID NO:7, or SEQ ID NO:8; and
administering the therapeutically-effective amount of the peptide to the eye of the mammal.

2. The method of claim 1 wherein the peptide consists of SEQ ID NO:6.

3. The method of claim 1 wherein the peptide consists of SEQ ID NO:7.

4. The method of claim 1 wherein the peptide consists of SEQ ID NO:8.

5. The method of claim 1 wherein the infection is bacterial keratitis.

6. The method of claim 5 wherein the bacterial keratitis is caused by *Pseudomonas aeruginosa*.

7. The method of claim 5 wherein the bacterial keratitis is caused by *Staphylococcus aureus*.

8. The method of claim 1 wherein the infection is bacterial conjunctivitis.

9. The method of claim 1 wherein the infection is endophthalmitis.

10. The method of claim 1 wherein the infection is blebitis.

* * * * *

SEQUENCE LISTING

```
<160> NUMBER OF SEQ ID NOS: 20

<210> SEQ ID NO 1
<211> LENGTH: 222
<212> TYPE: PRT
<213> ORGANISM: Homo sapiens

<400> SEQUENCE: 1

Ile Val Gly Gly Arg Lys Ala Arg Pro Arg Gln Phe Pro Phe Leu Ala
1               5                   10                  15

Ser Ile Gln Asn Gln Gly Arg His Phe Cys Gly Gly Ala Leu Ile His
            20                  25                  30

Ala Arg Phe Val Met Thr Ala Ala Ser Cys Phe Gln Ser Gln Asn Pro
        35                  40                  45
```

```
Gly Val Ser Thr Val Val Leu Gly Ala Tyr Asp Leu Arg Arg Glu
    50                  55                  60

Arg Gln Ser Arg Gln Thr Phe Ser Ile Ser Ser Met Ser Glu Asn Gly
65                  70                  75                  80

Tyr Asp Pro Gln Gln Asn Leu Asn Asp Leu Met Leu Leu Gln Leu Asp
                85                  90                  95

Arg Glu Ala Asn Leu Thr Ser Ser Val Thr Ile Leu Pro Leu Pro Leu
                100                 105                 110

Gln Asn Ala Thr Val Glu Ala Gly Thr Arg Cys Gln Val Ala Gly Trp
                115                 120                 125

Gly Ser Gln Arg Ser Gly Gly Arg Leu Ser Arg Phe Pro Arg Phe Val
    130                 135                 140

Asn Val Thr Val Thr Pro Glu Asp Gln Cys Arg Pro Asn Asn Val Cys
145                 150                 155                 160

Thr Gly Val Leu Thr Arg Arg Gly Gly Ile Cys Asn Gly Asp Gly Gly
                165                 170                 175

Thr Pro Leu Val Cys Glu Gly Leu Ala His Gly Val Ala Ser Phe Ser
                180                 185                 190

Leu Gly Pro Cys Gly Arg Gly Pro Asp Phe Phe Thr Arg Val Ala Leu
    195                 200                 205

Phe Arg Asp Trp Ile Asp Gly Val Leu Asn Asn Pro Gly Pro
    210                 215                 220

<210> SEQ ID NO 2
<211> LENGTH: 199
<212> TYPE: PRT
<213> ORGANISM: Homo sapiens

<400> SEQUENCE: 2

Asn Gln Gly Arg His Phe Cys Gly Gly Ala Leu Ile His Ala Arg Phe
1               5                   10                  15

Val Met Thr Ala Ala Ser Cys Phe Gln Ser Gln Asn Pro Gly Val Ser
                20                  25                  30

Thr Val Val Leu Gly Ala Tyr Asp Leu Arg Arg Arg Glu Arg Gln Ser
                35                  40                  45

Arg Gln Thr Phe Ser Ile Ser Ser Met Ser Glu Asn Gly Tyr Asp Pro
    50                  55                  60

Gln Gln Asn Leu Asn Asp Leu Met Leu Leu Gln Leu Asp Arg Glu Ala
65                  70                  75                  80

Asn Leu Thr Ser Ser Val Thr Ile Leu Pro Leu Pro Leu Gln Asn Ala
                85                  90                  95

Thr Val Glu Ala Gly Thr Arg Cys Gln Val Ala Gly Trp Gly Ser Gln
                100                 105                 110

His Ser Gly Gly Arg Leu Ser Arg Phe Pro Arg Phe Val Asn Val Thr
            115                 120                 125

Val Thr Pro Glu Asp Gln Cys Arg Pro Asn Asn Val Cys Thr Gly Val
            130                 135                 140

Leu Thr Arg Arg Gly Gly Ile Cys Asn Gly Asp Gly Gly Thr Pro Leu
145                 150                 155                 160

Val Cys Glu Gly Leu Ala His Gly Val Ala Ser Phe Ser Leu Gly Pro
                165                 170                 175

Cys Gly Arg Gly Pro Asp Phe Phe Thr Arg Val Ala Leu Phe Arg Asp
            180                 185                 190

Trp Ile Asp Gly Val Leu Asn
```

195

<210> SEQ ID NO 3
<211> LENGTH: 25
<212> TYPE: PRT
<213> ORGANISM: Artificial sequence
<220> FEATURE:
<223> OTHER INFORMATION: Completely synthesized

<400> SEQUENCE: 3

Asn Gln Gly Arg His Phe Cys Gly Gly Ala Leu Ile His Ala Arg Phe
1               5                   10                  15

Val Met Thr Ala Ala Ser Cys Phe Gln
            20                  25

<210> SEQ ID NO 4
<211> LENGTH: 20
<212> TYPE: PRT
<213> ORGANISM: Artificial sequence
<220> FEATURE:
<223> OTHER INFORMATION: Completely synthesized

<400> SEQUENCE: 4

Arg His Phe Cys Gly Gly Ala Leu Ile His Ala Arg Phe Val Met Thr
1               5                   10                  15

Ala Ala Ser Cys
            20

<210> SEQ ID NO 5
<211> LENGTH: 21
<212> TYPE: PRT
<213> ORGANISM: Artificial sequence
<220> FEATURE:
<223> OTHER INFORMATION: Completely synthesized

<400> SEQUENCE: 5

Thr Ser Ser Val Thr Ile Leu Pro Leu Pro Leu Gln Asn Ala Thr Val
1               5                   10                  15

Glu Ala Gly Thr Arg
            20

<210> SEQ ID NO 6
<211> LENGTH: 27
<212> TYPE: PRT
<213> ORGANISM: Artificial sequence
<220> FEATURE:
<223> OTHER INFORMATION: Completely synthesized

<400> SEQUENCE: 6

Gly Thr Arg Cys Gln Val Ala Gly Trp Gly Ser Gln Arg Ser Gly Gly
1               5                   10                  15

Arg Leu Ser Arg Phe Pro Arg Phe Val Asn Val
            20                  25

<210> SEQ ID NO 7
<211> LENGTH: 20
<212> TYPE: PRT
<213> ORGANISM: Artificial sequence
<220> FEATURE:
<223> OTHER INFORMATION: Completely synthesized
<220> FEATURE:
<221> NAME/KEY: MISC_FEATURE
<222> LOCATION: (3)..(3)
<223> OTHER INFORMATION: phe or tyr
<220> FEATURE:
<221> NAME/KEY: MISC_FEATURE

```
<222> LOCATION: (5)..(5)
<223> OTHER INFORMATION: gly or ala
<220> FEATURE:
<221> NAME/KEY: MISC_FEATURE
<222> LOCATION: (6)..(6)
<223> OTHER INFORMATION: gly or ala
<220> FEATURE:
<221> NAME/KEY: MISC_FEATURE
<222> LOCATION: (7)..(7)
<223> OTHER INFORMATION: ala, leu, ile or val
<220> FEATURE:
<221> NAME/KEY: MISC_FEATURE
<222> LOCATION: (8)..(8)
<223> OTHER INFORMATION: ala, leu, ile or val
<220> FEATURE:
<221> NAME/KEY: MISC_FEATURE
<222> LOCATION: (9)..(9)
<223> OTHER INFORMATION: ala, leu, ile or val
<220> FEATURE:
<221> NAME/KEY: MISC_FEATURE
<222> LOCATION: (11)..(11)
<223> OTHER INFORMATION: ala, leu, ile or val
<220> FEATURE:
<221> NAME/KEY: MISC_FEATURE
<222> LOCATION: (13)..(13)
<223> OTHER INFORMATION: phe or tyr
<220> FEATURE:
<221> NAME/KEY: MISC_FEATURE
<222> LOCATION: (14)..(14)
<223> OTHER INFORMATION: ala, lue, ile or val
<220> FEATURE:
<221> NAME/KEY: MISC_FEATURE
<222> LOCATION: (16)..(16)
<223> OTHER INFORMATION: ser or thr
<220> FEATURE:
<221> NAME/KEY: MISC_FEATURE
<222> LOCATION: (17)..(17)
<223> OTHER INFORMATION: ala, leu, ile or val
<220> FEATURE:
<221> NAME/KEY: MISC_FEATURE
<222> LOCATION: (18)..(18)
<223> OTHER INFORMATION: ala, leu, ile or val
<220> FEATURE:
<221> NAME/KEY: MISC_FEATURE
<222> LOCATION: (19)..(19)
<223> OTHER INFORMATION: ser, thr, his, arg or lys
<220> FEATURE:
<221> NAME/KEY: MISC_FEATURE
<222> LOCATION: (20)..(20)
<223> OTHER INFORMATION: ser or thr

<400> SEQUENCE: 7

Arg His Xaa Cys Xaa Xaa Xaa Xaa Xaa His Xaa Arg Xaa Xaa Met Xaa
 1               5                  10                  15

Xaa Xaa Xaa Xaa
            20

<210> SEQ ID NO 8
<211> LENGTH: 20
<212> TYPE: PRT
<213> ORGANISM: Artificial sequence
<220> FEATURE:
<223> OTHER INFORMATION: Completely synthesized
<220> FEATURE:
<221> NAME/KEY: MISC_FEATURE
<222> LOCATION: (3)..(3)
<223> OTHER INFORMATION: phe or tyr
<220> FEATURE:
<221> NAME/KEY: MISC_FEATURE
<222> LOCATION: (4)..(4)
<223> OTHER INFORMATION: ser or thr
<220> FEATURE:
<221> NAME/KEY: MISC_FEATURE
<222> LOCATION: (5)..(5)
<223> OTHER INFORMATION: gly or ala
<220> FEATURE:
```

```
<221> NAME/KEY: MISC_FEATURE
<222> LOCATION: (6)..(6)
<223> OTHER INFORMATION: gly or ala
<220> FEATURE:
<221> NAME/KEY: MISC_FEATURE
<222> LOCATION: (7)..(7)
<223> OTHER INFORMATION: ala, leu, ile or val
<220> FEATURE:
<221> NAME/KEY: MISC_FEATURE
<222> LOCATION: (8)..(8)
<223> OTHER INFORMATION: ala, leu, ile or val
<220> FEATURE:
<221> NAME/KEY: MISC_FEATURE
<222> LOCATION: (9)..(9)
<223> OTHER INFORMATION: ala, leu, ile or val
<220> FEATURE:
<221> NAME/KEY: MISC_FEATURE
<222> LOCATION: (11)..(11)
<223> OTHER INFORMATION: ala, leu, ile or val
<220> FEATURE:
<221> NAME/KEY: MISC_FEATURE
<222> LOCATION: (13)..(13)
<223> OTHER INFORMATION: phe or tyr
<220> FEATURE:
<221> NAME/KEY: MISC_FEATURE
<222> LOCATION: (14)..(14)
<223> OTHER INFORMATION: ala, leu, ile or val
<220> FEATURE:
<221> NAME/KEY: MISC_FEATURE
<222> LOCATION: (16)..(16)
<223> OTHER INFORMATION: ser or thr
<220> FEATURE:
<221> NAME/KEY: MISC_FEATURE
<222> LOCATION: (17)..(17)
<223> OTHER INFORMATION: ala, leu, ile or val
<220> FEATURE:
<221> NAME/KEY: MISC_FEATURE
<222> LOCATION: (18)..(18)
<223> OTHER INFORMATION: ala, leu, ile or val
<220> FEATURE:
<221> NAME/KEY: MISC_FEATURE
<222> LOCATION: (19)..(19)
<223> OTHER INFORMATION: ser, thr, his, arg or lys

<400> SEQUENCE: 8

Arg His Xaa Xaa Xaa Xaa Xaa Xaa Xaa His Xaa Arg Xaa Xaa Met Xaa
1               5                   10                  15

Xaa Xaa Xaa Cys
            20

<210> SEQ ID NO 9
<211> LENGTH: 24
<212> TYPE: DNA
<213> ORGANISM: Artificial sequence
<220> FEATURE:
<223> OTHER INFORMATION: Completely synthesized

<400> SEQUENCE: 9
cagaatcaag gcaggcactt ctgc                                          24

<210> SEQ ID NO 10
<211> LENGTH: 24
<212> TYPE: DNA
<213> ORGANISM: Artificial sequence
<220> FEATURE:
<223> OTHER INFORMATION: Completely synthesized

<400> SEQUENCE: 10
gagaacacca tcgatcgagt ctcg                                          24

<210> SEQ ID NO 11
<211> LENGTH: 20
```

```
<212> TYPE: DNA
<213> ORGANISM: Artificial sequence
<220> FEATURE:
<223> OTHER INFORMATION: Completely synthesized

<400> SEQUENCE: 11
gtccccctca aaagtcatcc                                              20

<210> SEQ ID NO 12
<211> LENGTH: 20
<212> TYPE: DNA
<213> ORGANISM: Artificial sequence
<220> FEATURE:
<223> OTHER INFORMATION: Completely synthesized

<400> SEQUENCE: 12
aaccccattc agcgtcacgt                                              20

<210> SEQ ID NO 13
<211> LENGTH: 20
<212> TYPE: DNA
<213> ORGANISM: Artificial sequence
<220> FEATURE:
<223> OTHER INFORMATION: Completely synthesized

<400> SEQUENCE: 13
agtggtggcc tcgtgaatgg                                              20

<210> SEQ ID NO 14
<211> LENGTH: 20
<212> TYPE: DNA
<213> ORGANISM: Artificial sequence
<220> FEATURE:
<223> OTHER INFORMATION: Completely synthesized

<400> SEQUENCE: 14
ctgtgtctcc tgtctccgct                                              20

<210> SEQ ID NO 15
<211> LENGTH: 20
<212> TYPE: DNA
<213> ORGANISM: Artificial sequence
<220> FEATURE:
<223> OTHER INFORMATION: Completely synthesized

<400> SEQUENCE: 15
ttgcagcaca atgtcctctc                                              20

<210> SEQ ID NO 16
<211> LENGTH: 20
<212> TYPE: DNA
<213> ORGANISM: Artificial sequence
<220> FEATURE:
<223> OTHER INFORMATION: Completely synthesized

<400> SEQUENCE: 16
agcacagtgg caactacacg                                              20

<210> SEQ ID NO 17
<211> LENGTH: 20
<212> TYPE: DNA
<213> ORGANISM: Artificial sequence
<220> FEATURE:
<223> OTHER INFORMATION: Completely synthesized

<400> SEQUENCE: 17
```

```
                                       -continued
agaagaagct tgccctatgc                                               20

<210> SEQ ID NO 18
<211> LENGTH: 22
<212> TYPE: DNA
<213> ORGANISM: Artificial sequence
<220> FEATURE:
<223> OTHER INFORMATION: Completely synthesized

<400> SEQUENCE: 18
aggctggaat aggagcactc ca                                            22

<210> SEQ ID NO 19
<211> LENGTH: 19
<212> TYPE: DNA
<213> ORGANISM: Artificial sequence
<220> FEATURE:
<223> OTHER INFORMATION: Completely synthesized

<400> SEQUENCE: 19
tacctcatga agatcctca                                                19

<210> SEQ ID NO 20
<211> LENGTH: 19
<212> TYPE: DNA
<213> ORGANISM: Artificial sequence
<220> FEATURE:
<223> OTHER INFORMATION: Completely synthesized

<400> SEQUENCE: 20
ttcgtggatg ccacaggac                                                19
```